United States Patent
Nagai et al.

(10) Patent No.: US 10,918,846 B2
(45) Date of Patent: Feb. 16, 2021

(54) IMPACTING TYPE APPLICATOR FOR MICRONEEDLE PATCH AND LEADING END MEMBER

(71) Applicant: Labo Juversa Co., Ltd., Hokkaido (JP)

(72) Inventors: Hiroyuki Nagai, Kyoto (JP); Risa Nakaoka, Kyoto (JP); Ichiro Ono, Hokkaido (JP); Kanji Takada, Kyoto (JP)

(73) Assignee: Labo Juversa Co., Ltd., Sappaoro (JP)

( * ) Notice: Subject to any disclaimer, the term of this patent is extended or adjusted under 35 U.S.C. 154(b) by 372 days.

(21) Appl. No.: 15/745,250

(22) PCT Filed: Jul. 11, 2016

(86) PCT No.: PCT/JP2016/070439
§ 371 (c)(1),
(2) Date: Nov. 26, 2018

(87) PCT Pub. No.: WO2017/014091
PCT Pub. Date: Jan. 26, 2017

(65) Prior Publication Data
US 2019/0083769 A1 Mar. 21, 2019

(30) Foreign Application Priority Data

Jul. 22, 2015 (JP) .................... 2015-145084

(51) Int. Cl.
*A61M 37/00* (2006.01)

(52) U.S. Cl.
CPC . *A61M 37/0015* (2013.01); *A61M 2037/0023* (2013.01); *A61M 2202/30* (2013.01); *A61M 2205/0288* (2013.01)

(58) Field of Classification Search
CPC ........ A61M 5/2033; A61M 2005/1585; A61M 37/0015; A61M 2037/0061; A61M 2037/0026; A61B 2017/925
See application file for complete search history.

(56) References Cited

U.S. PATENT DOCUMENTS

| | | | |
|---|---|---|---|
| 6,293,925 B1* | 9/2001 | Safabash | A61M 5/158 604/136 |
| 2006/0095061 A1* | 5/2006 | Trautman | A61B 5/150824 606/185 |
| 2013/0226098 A1* | 8/2013 | Tokumoto | A61M 37/0015 604/228 |

FOREIGN PATENT DOCUMENTS

| | | |
|---|---|---|
| AU | 2015200337 A1 | 2/2015 |
| JP | 10-504474 | 5/1998 |

(Continued)

OTHER PUBLICATIONS

Labo Juversa Co., Ltd., Notification of Transmittal of Translation of the International Preliminary Report on Patentability, 9 pages, Feb. 1, 2018.

*Primary Examiner* — Laura A Bouchelle
(74) *Attorney, Agent, or Firm* — Ballard Spahr LLP

(57) ABSTRACT

To achieve stable administration of a medicine into a dermis by improving the operability of a device that inserts a microneedle into a skin. An impacting type applicator (1) for a microneedle patch is an applicator that applies a microneedle patch (3) to a skin includes a main body (5), a spring expanding/compressing lever (7), a resilient body (9), a lock mechanism (11), and a piercing switch (13). The spring expanding/compressing lever (7) is movably attached to the main body (5), and the microneedle patch (3) can be attached to a leading end of the spring expanding/compressing lever (7). The resilient body (9) is a member that imparts a biasing force to the spring expanding/compressing lever (Continued)

(7). The lock mechanism (11) is a mechanism that locks the spring expanding/compressing lever (7) in a state where the resilient body (9) exerts the biasing force on the main body (5). The piercing switch (13) is a member that releases the engagement between the lock mechanism (11) and the spring expanding/compressing lever (7). In addition, a biasing force imparting mechanism (121) further imparts a biasing force to the spring expanding/compressing lever (7) in a state where the spring expanding/compressing lever (7) is moved toward the leading end of the main body (5) and thereby presses the microneedle patch (3) against the skin.

18 Claims, 17 Drawing Sheets

(56) References Cited

FOREIGN PATENT DOCUMENTS

| | | |
|---|---|---|
| JP | 2004-510530 A | 4/2004 |
| JP | 2004-510534 | 4/2004 |
| JP | 2006-500973 | 1/2006 |
| JP | 2007-509706 | 4/2007 |
| JP | 2007-509706 A | 4/2007 |
| JP | 2014-509208 | 4/2014 |
| JP | 2014-83199 | 5/2014 |
| JP | 5663792 | 12/2014 |
| WO | WO 02/30301 A1 | 4/2002 |
| WO | WO 2002/30281 | 4/2002 |
| WO | WO 2005/044333 | 5/2005 |
| WO | WO 2013/051568 | 4/2013 |
| WO | WO 2014-002872 | 1/2014 |
| WO | WO 2014/193725 | 12/2014 |
| WO | WO 2015/040697 | 3/2015 |

\* cited by examiner

[Figure 1]
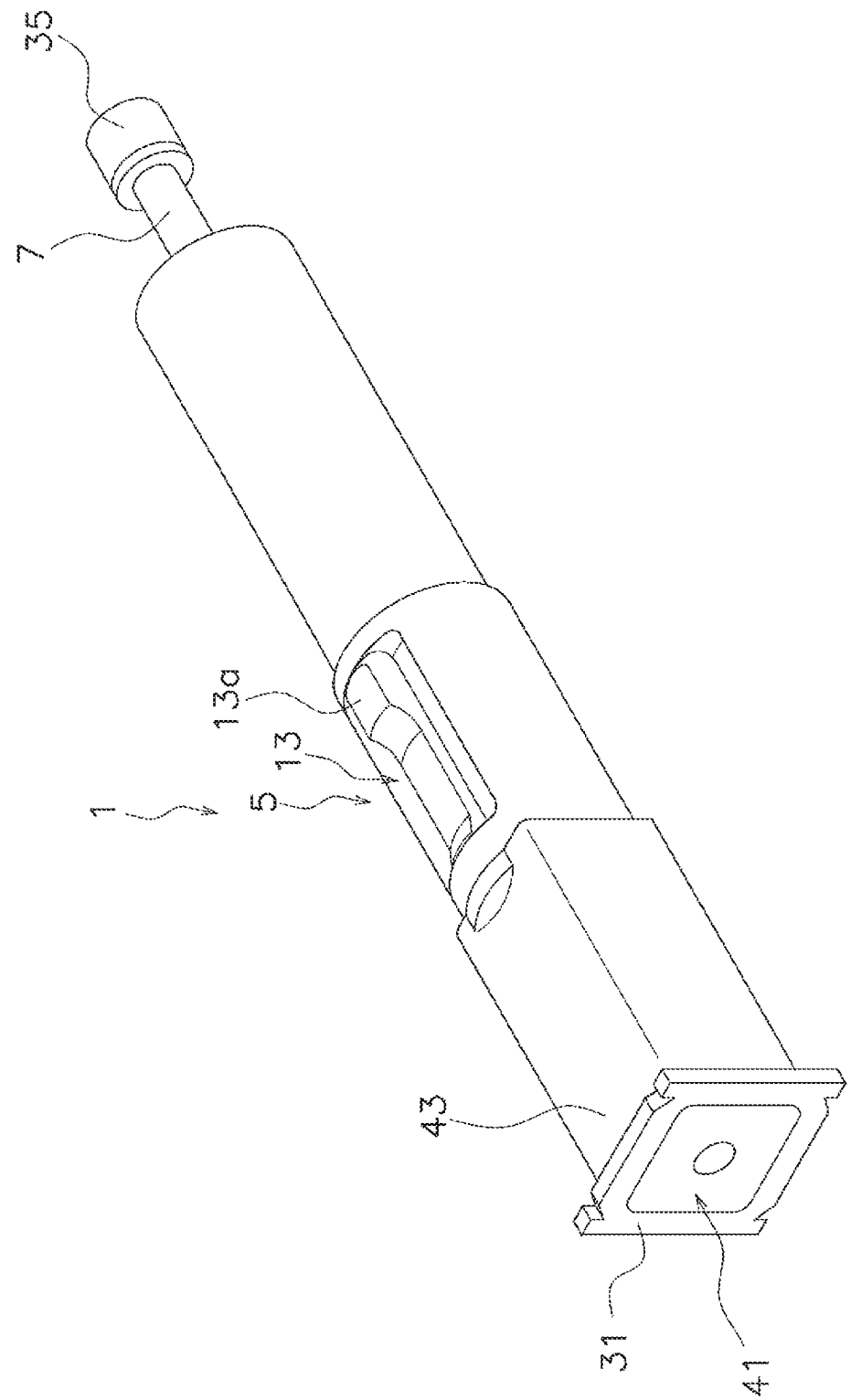

[Figure 2]
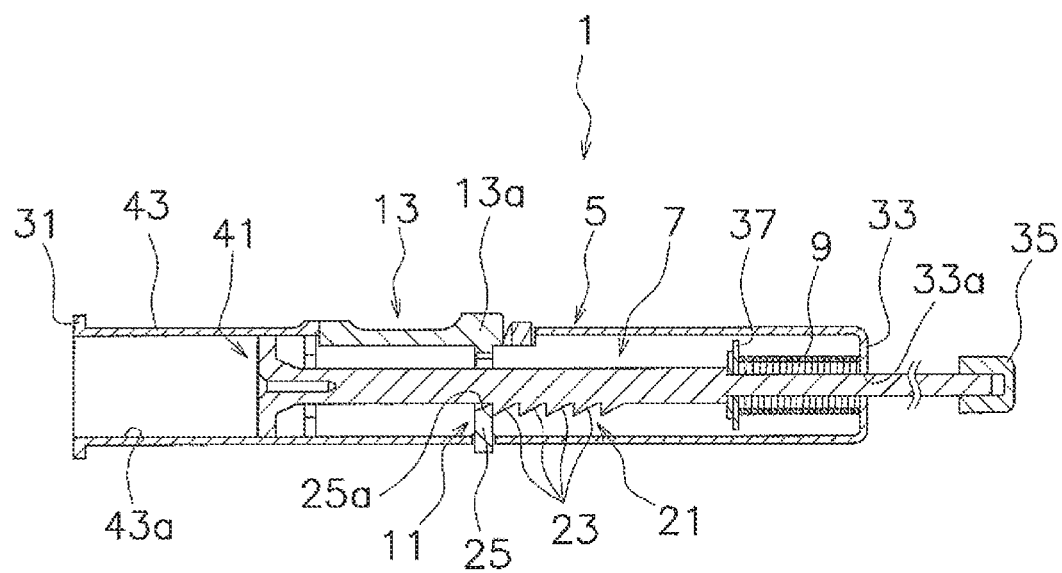
[Figure 3]
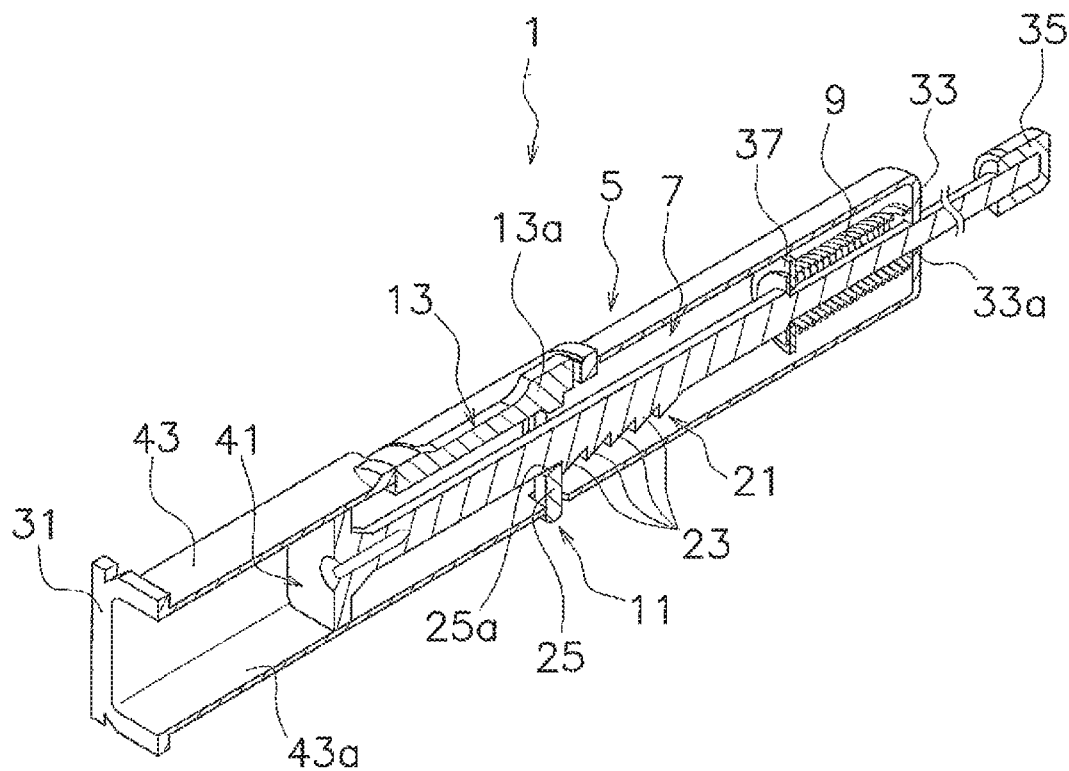

[Figure 4]
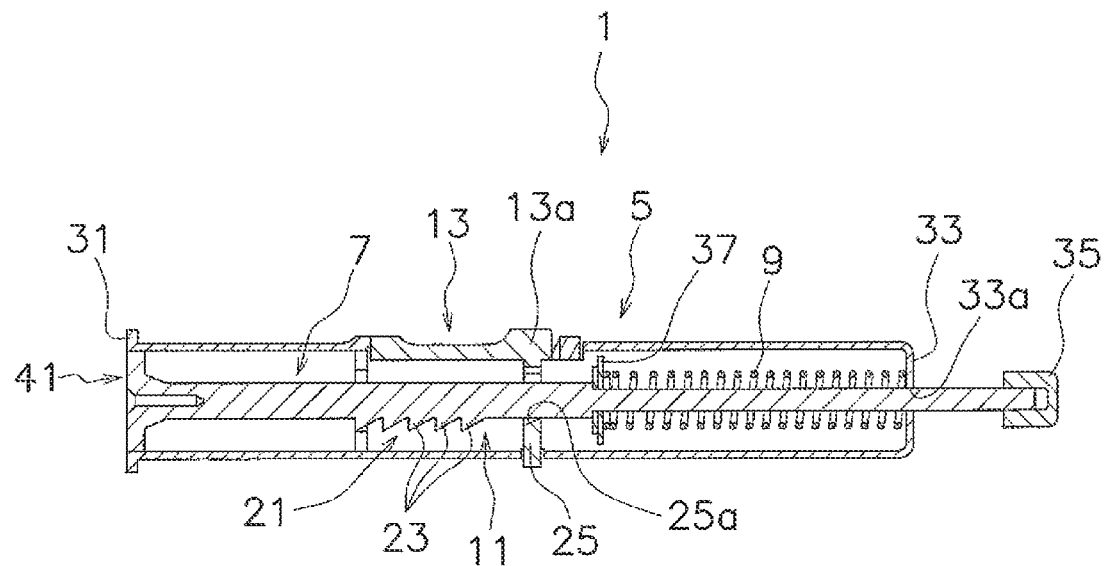
[Figure 5]
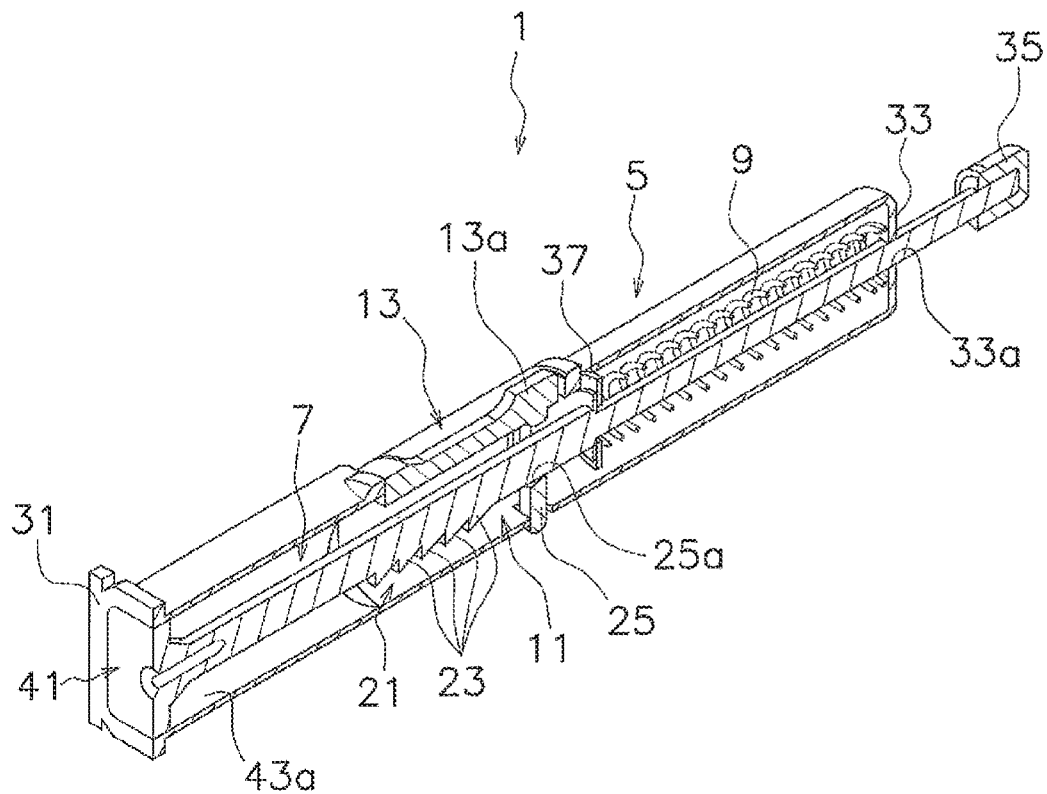

[Figure 6]
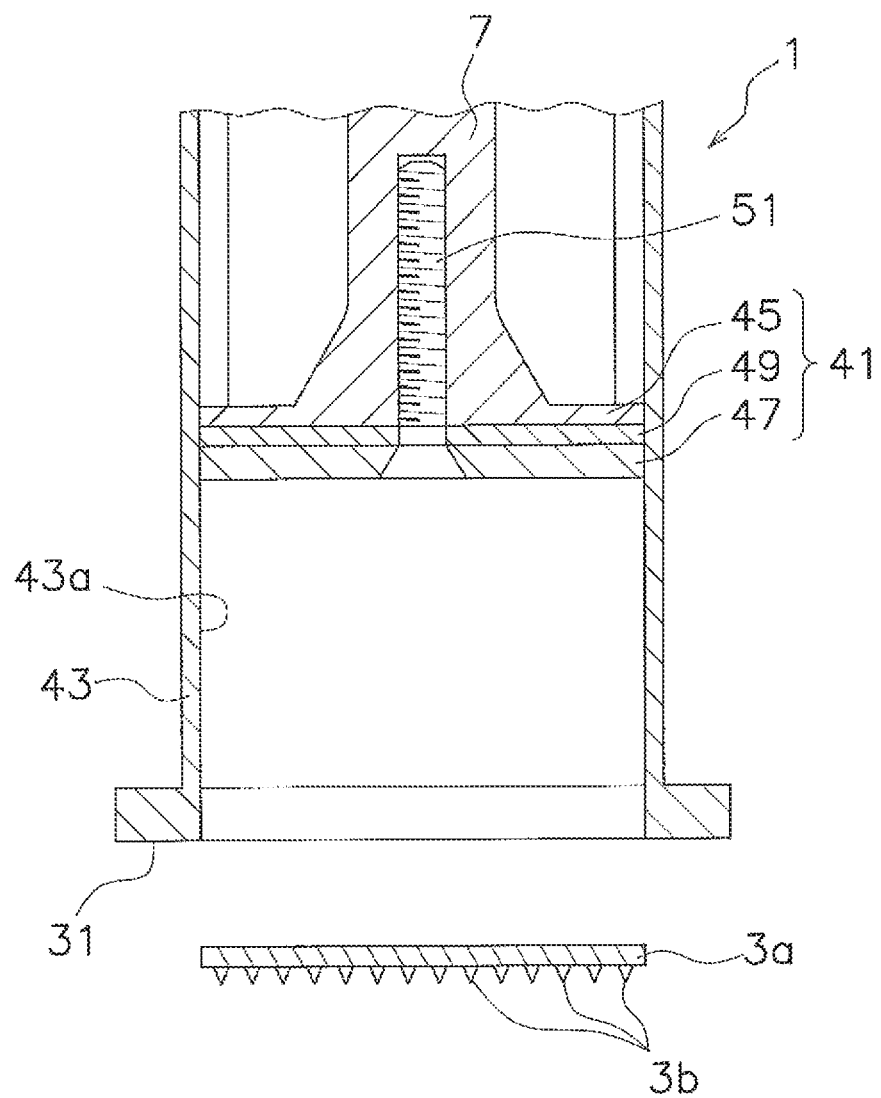

[Figure 7]
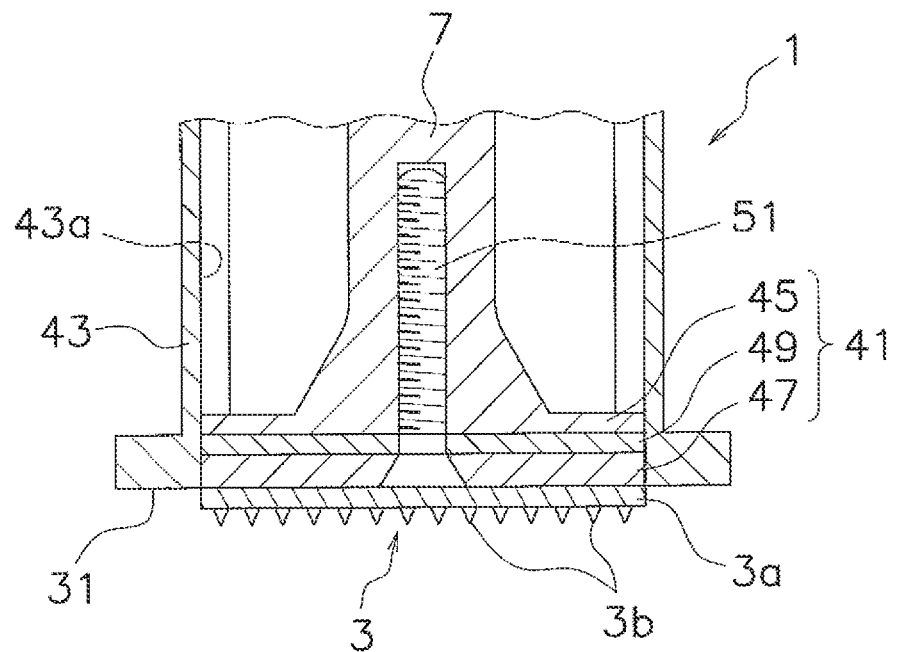

[Figure 8]
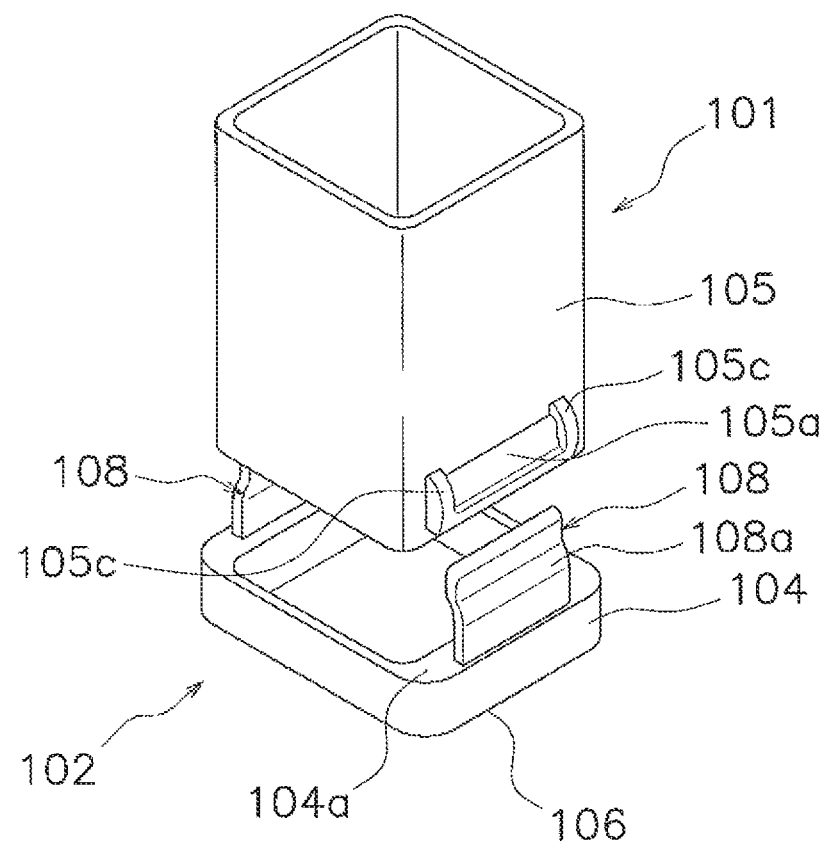

[Figure 9]
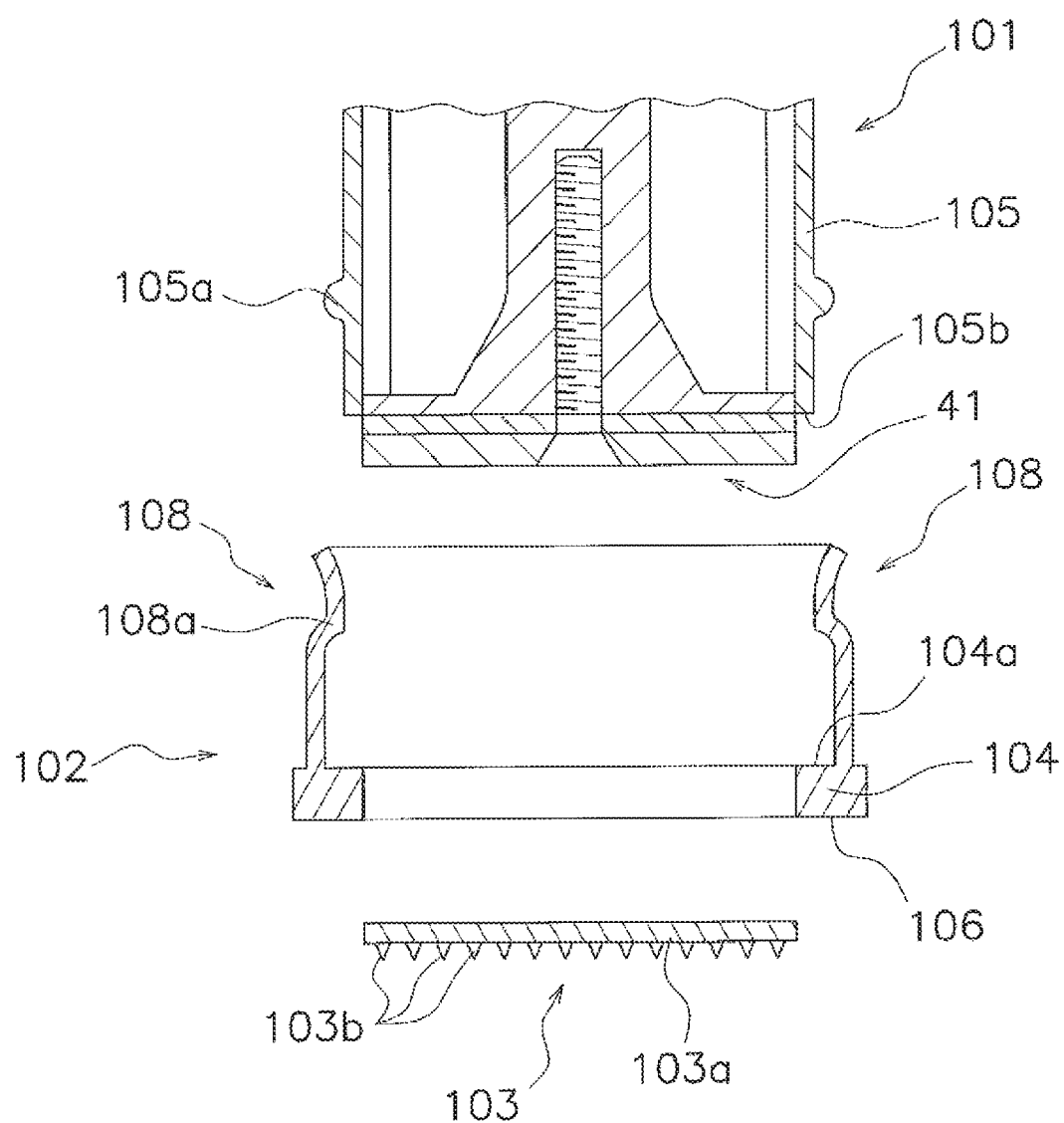

[Figure 10]
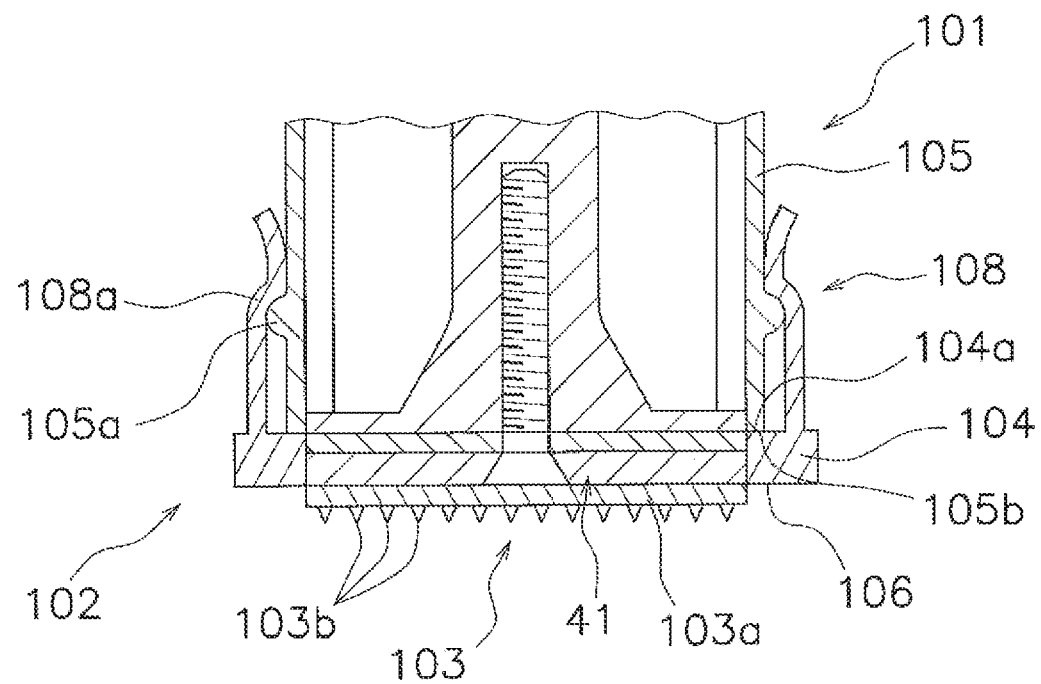

[Figure 11]
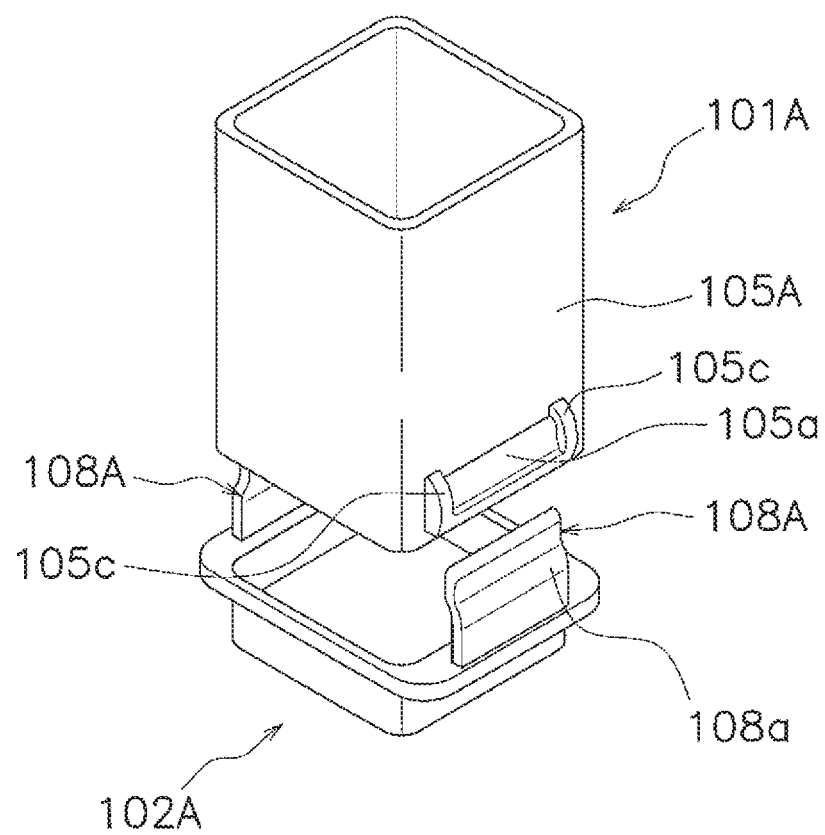

[Figure 12]
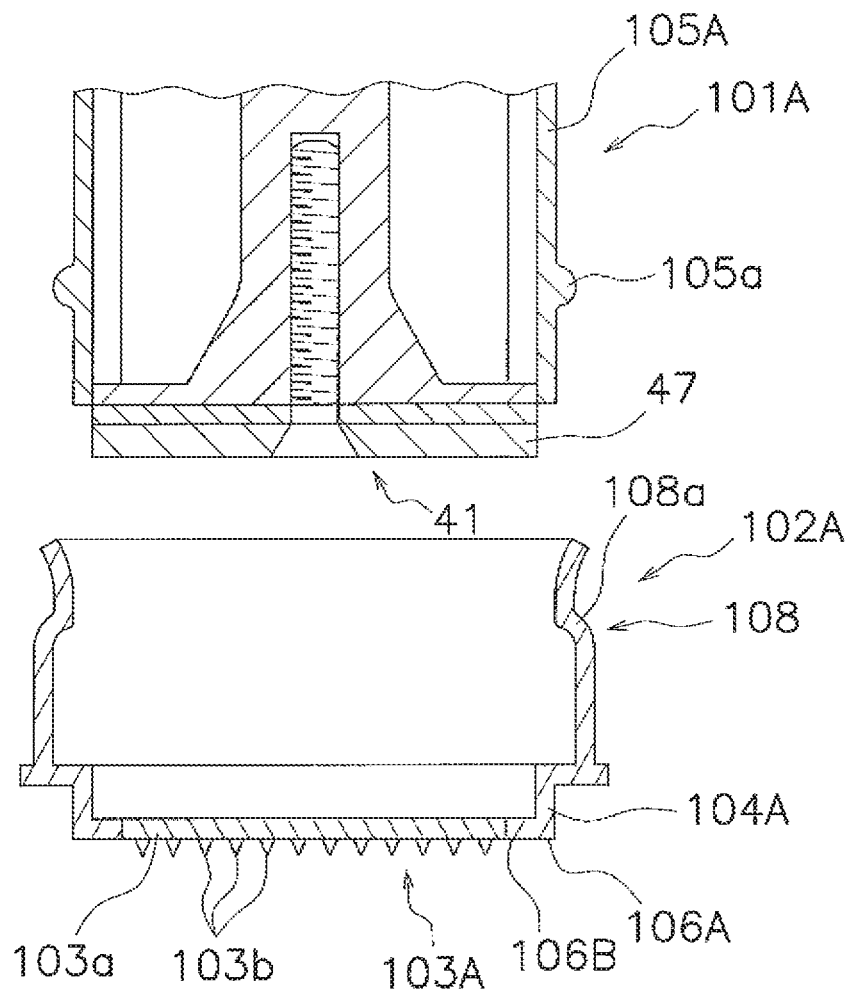

[Figure 13]
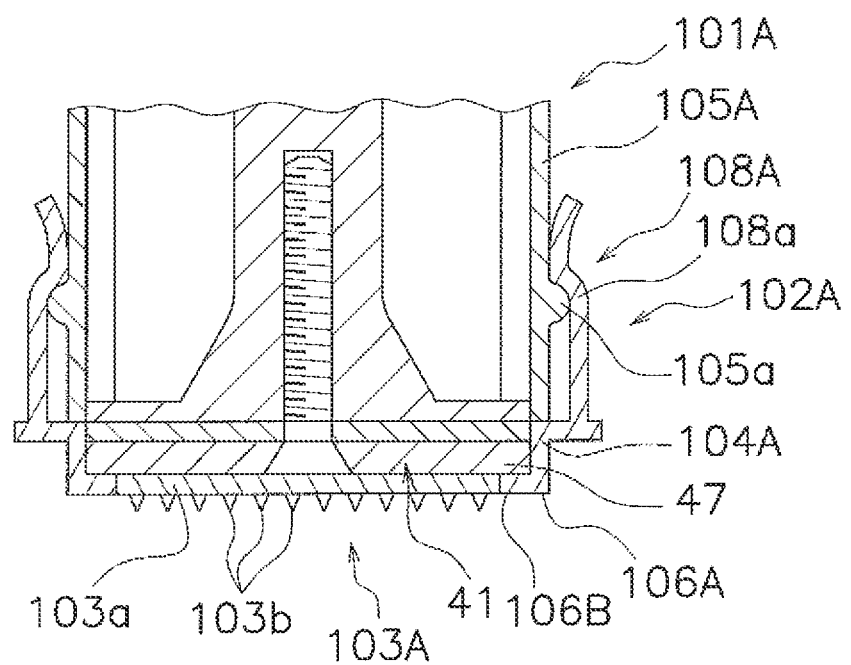

[Figure 14]
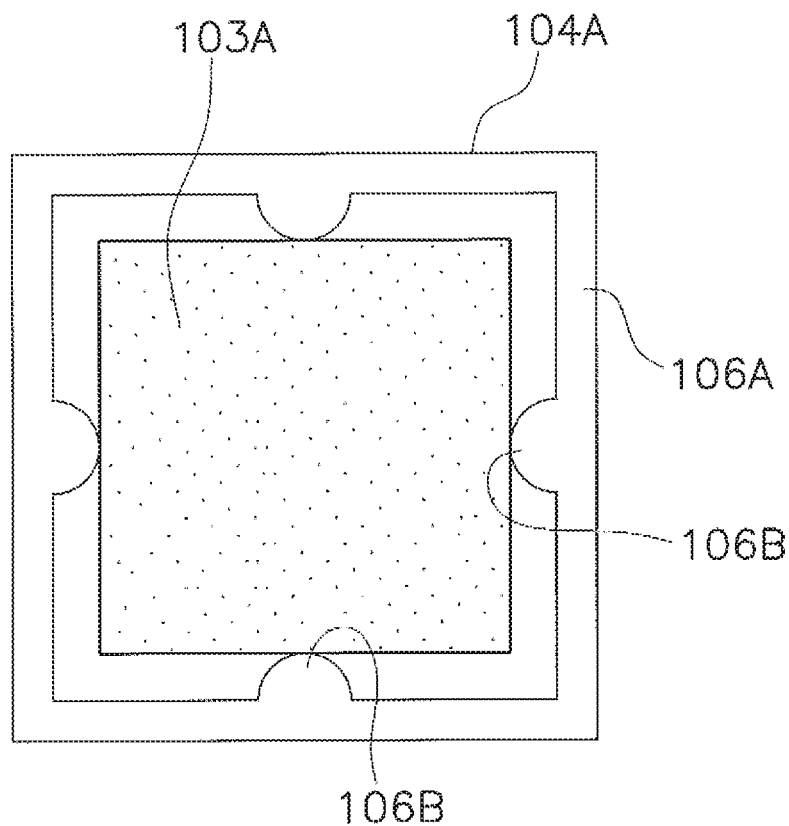
[Figure 15]
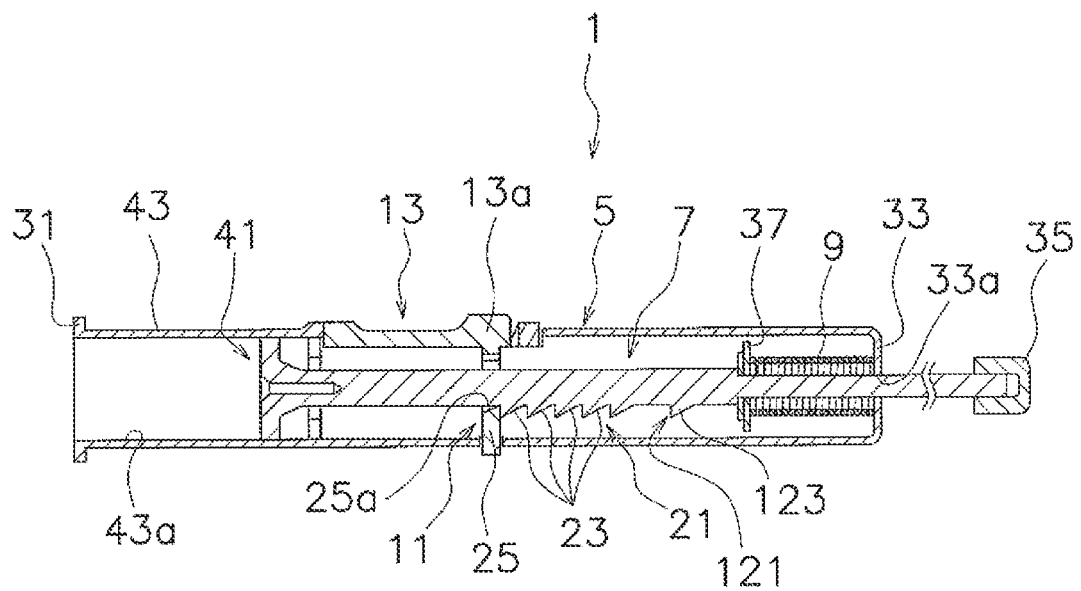

[Figure 16]
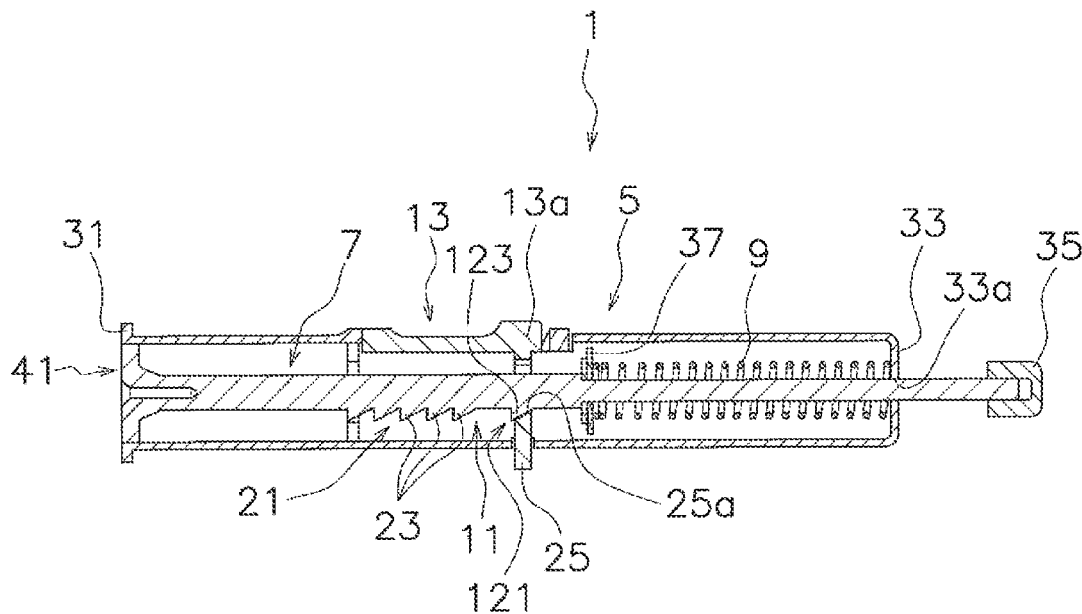
[Figure 17]
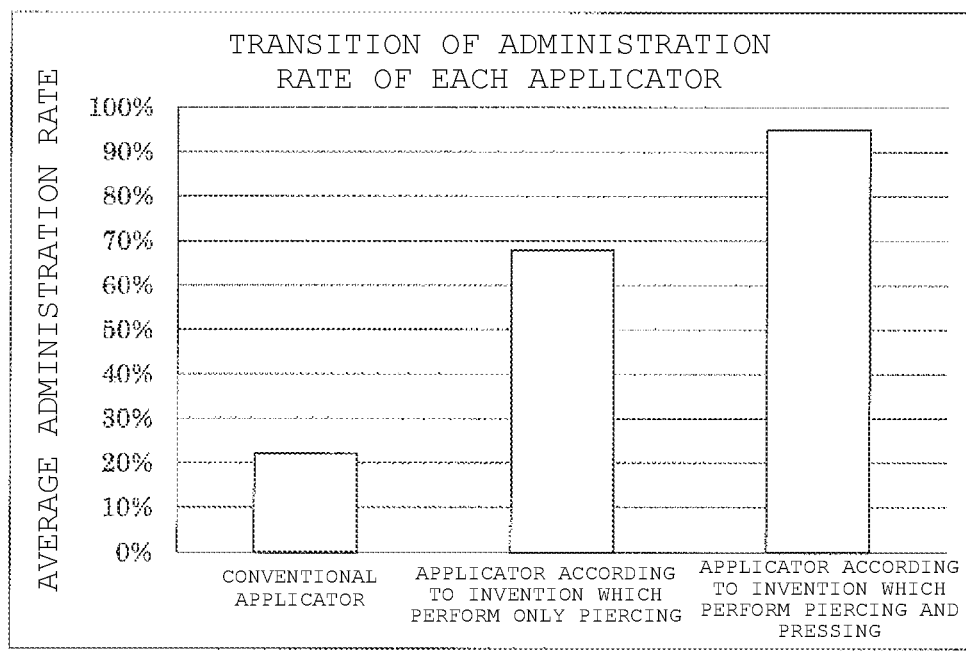

[Figure 18]
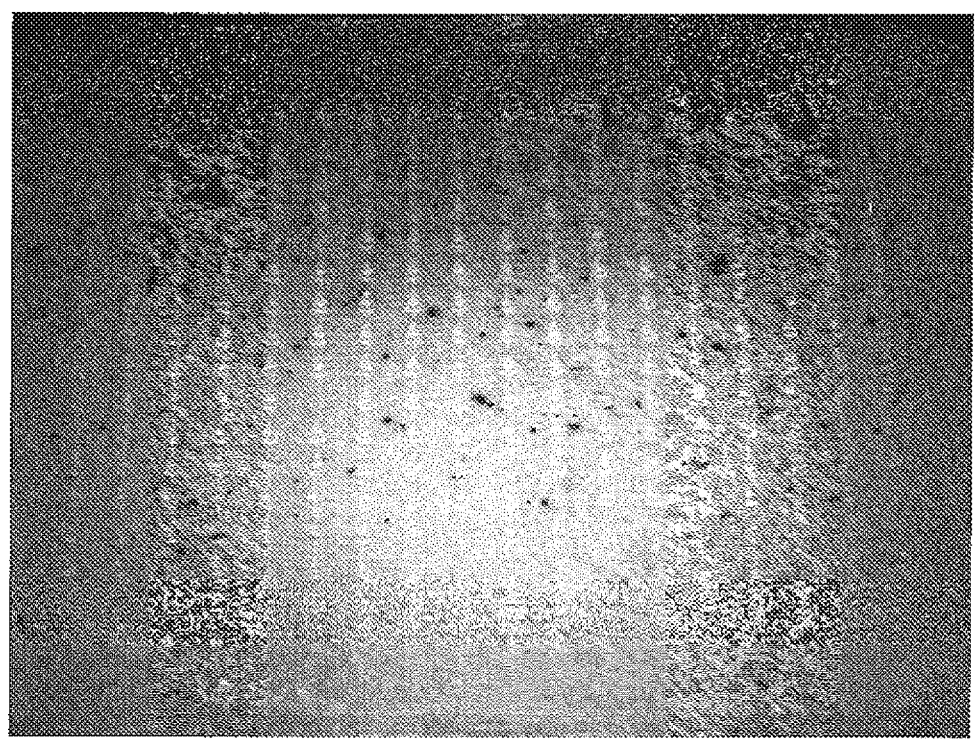

[Figure 19]
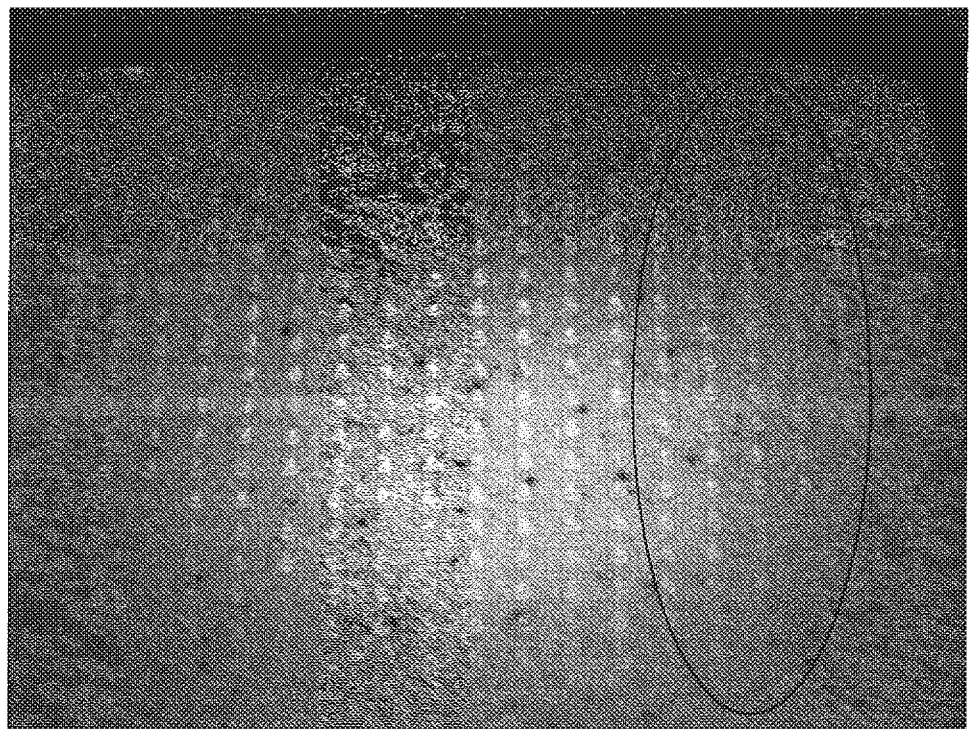

[Figure 20]
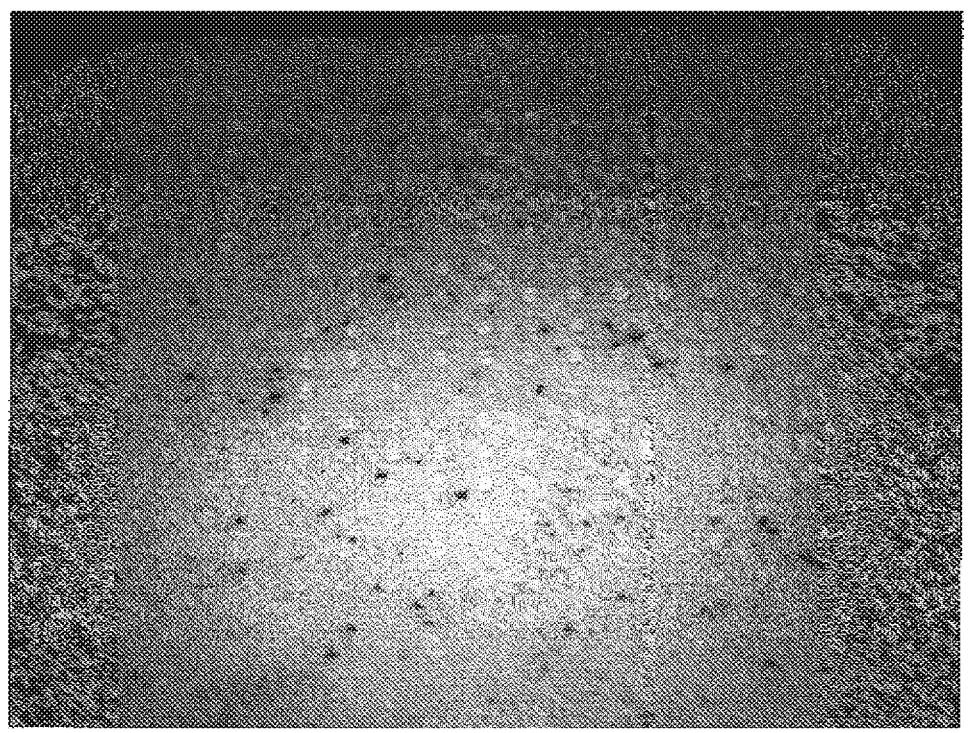
[Figure 21]
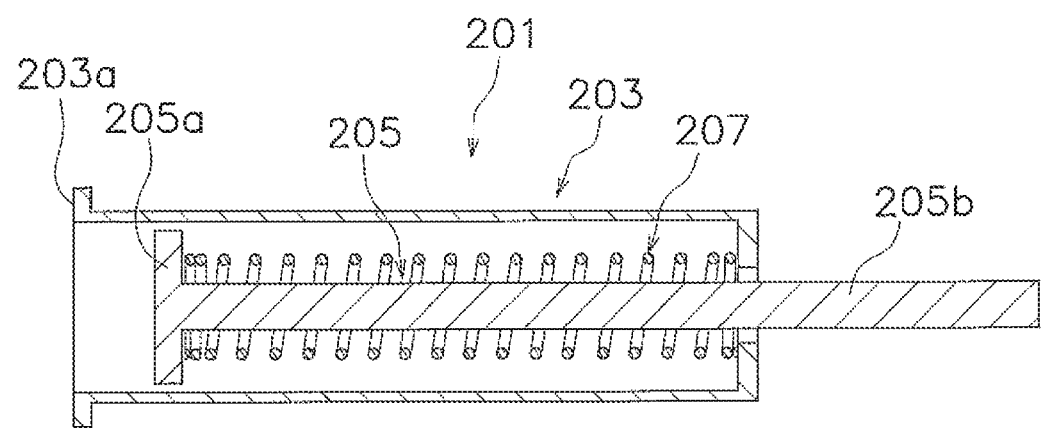

[Figure 22]
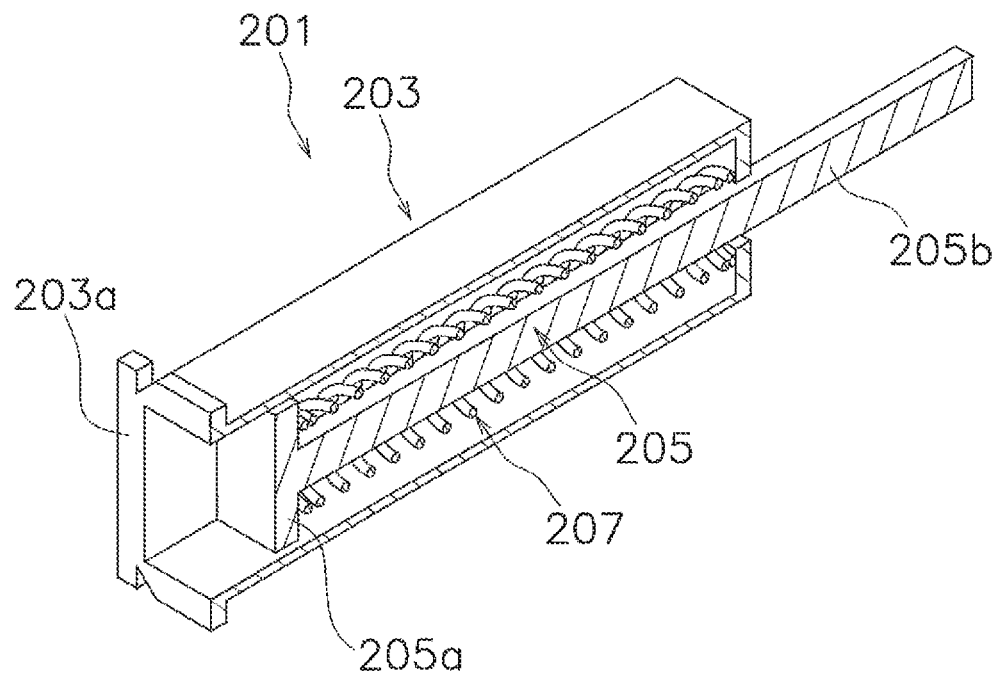

US 10,918,846 B2

IMPACTING TYPE APPLICATOR FOR MICRONEEDLE PATCH AND LEADING END MEMBER

TECHNICAL FIELD

The present invention relates to an impacting type applicator for a microneedle patch and a leading end member.

BACKGROUND ART

The human skin consists of the cornified layer having a layered structure having a thickness of about 10 to 30 μm, the epidermal layer having a thickness of about 50 to 200 μm and the dermal layer having a thickness of about 2 to 5 mm. Of these layers, the cornified layer and the epidermis layer each have a strong barrier function and hence it is hardly expectable that a medicine having a high molecular weight is adsorbed intradermally. On the other hand, it is characteristic of the dermis layer that a dense capillary network is present in its superficial layer referred to as a papillary layer. In addition, as is known, Langerhans cells, which play an important role in immune sensitization, are present in the epidermis layer, and the early stage of the immune sensitization occurs with substances which are present in the epidermis and in the shallow layer of the dermis as well. In this respect, to administer a medicine intradermally effectively, it is desirable to administer the medicine directly to the dermis layer. As a method of enabling such medicine administration, a microneedle patch having a large number of microneedles is used.

The microneedle patch has a substrate and a plurality of microneedles formed on one surface of the substrate. The length of the microneedle is equal to or greater than 30 μm, for example. Once the microneedle patch is applied to the skin, sharp tip end parts of the microneedles locally break the solid cornified layer, so that large parts of the microneedles penetrate through the epidermis and are inserted into the dermis, and the medicine contained in the microneedles can be properly administered to the dermis layer.

Devices for effectively inserting microneedles into the skin (that is, aid equipment) have been developed (see Patent Document 1, for example).

As such a device, there has been proposed an impacting type applicator having a structure that uses the resilient force of a spring to insert microneedles into the skin.

A conventional impacting type applicator will be described with reference to FIGS. 21 and 22. FIG. 21 is a cross-sectional view of the conventional applicator. FIG. 22 is a perspective cross-sectional view of the conventional applicator. A conventional applicator 201 is a device designed to press a microneedle patch against a skin to insert a microneedle into a dermis. More specifically, the applicator 201 can produce a biasing force that is high enough to pierce the microneedle patch into the skin. The applicator 201 has a main body 203. The main body 203 is a cylindrical member. The main body 203 has a contact part 203a at a leading end thereof. More specifically, the contact part 203a is a frame-shaped part that surrounds an opening at the leading end of the main body 203.

The applicator 201 has a spring expanding/compressing lever 205. The spring expanding/compressing lever 205 is attached to the main body 203 in such a manner that the spring expanding/compressing lever 205 is movable along the longitudinal direction of the main body 203. More specifically, the spring expanding/compressing lever 205 is disposed in the main body 203. The microneedle patch can be attached to a leading end 205a of the spring expanding/compressing lever 205. The spring expanding/compressing lever 205 extends in the main body 5. A rear end 205b of the spring expanding/compressing lever 205 protrudes from a through-hole in a rear end wall of the main body 203.

The applicator 201 has a resilient body 207. The resilient body 207 is a member intended to impart a biasing force to the spring expanding/compressing lever 7. The resilient body 207 allows the microneedle to be pierced into the skin to a predetermined depth with reliability. More specifically, the resilient body 207 is disposed in the main body 203 and imparts a biasing force to the spring expanding/compressing lever 205 in a state where the resilient body 207 is compressed in the longitudinal direction of the main body. The resilient body 207 can be compressed between the rear end wall of the main body 203 and the spring expanding/compressing lever 205.

PRIOR ART DOCUMENTS

Patent Documents

Patent Document 1: Japanese Patent No. 5663792

SUMMARY OF THE INVENTION

Object to be Solved by the Invention

However, for example, the method of inserting the microneedle to the skin using the applicator 201 described above, which is a device that uses the resilient force of a spring, requires an operation of pulling the spring expanding/compressing lever 205 by hands to compress the resilient body 207 to produce a resilient force. Therefore, the amount of compression of the resilient body 207 varies from operation to operation. That is, it is difficult to consistently produce an appropriate load. Thus, the microneedle of the microneedle is often insufficiently inserted into the dermis of the skin, and as a result, it is difficult to stably administer a medicine into dermis.

An object of the present invention is to achieve stable administration of a medicine into the dermis by means of improving the operability of a device that inserts a microneedle into a skin. The present invention allows reliable administration of a medicine that has been confirmed to be effective when directly administered into the dermis, which has an extremely important meaning from the viewpoint of making it possible for the administered medicine to exhibit its effects. In addition, the present invention allows easy and stable administration, into the dermis, of a medicine contained in a microneedle, and the medicine disperses into the dermis to exhibits its initial effect effectively. In addition, a medicine which is intended to be absorbed into the blood vessels of the whole body to exhibit its desired effect, can be administered into the dermis and then absorbed from the dense capillary network that are present in the dermal papillary layer to the blood vessels of the whole body where it exhibits its desired effect. In this respect, too, it is extremely important to establish a technique of reliably administering into the dermis the full dosage of the medicine applied to the microneedle.

Means to Solve the Object

In the following, a plurality of aspects will be described as means for solving the problems. These aspects can be arbitrarily combined with each other as required.

An impacting type applicator for a microneedle patch according to the present invention is an impacting type applicator that applies a microneedle patch to a skin by pressing the microneedle patch against the skin, comprising a main body, an actuator, a resilient body, a lock mechanism, and a releasing member.

The actuator is movably attached to the main body, and the microneedle patch is capable of being attached to a leading end of the actuator.

The resilient body is a member that imparts a biasing force to the actuator.

The lock mechanism is a mechanism that locks the actuator in a state where the resilient body exerts the biasing force on the main body.

The releasing member is a member that releases an engagement between the lock mechanism and the actuator.

With this applicator, the microneedle patch is first attached to the leading end of the actuator, and the lock mechanism then locks the actuator in a state where the resilient body exerts a biasing force on the main body. In this state, the applicator is placed at an appropriate position in an appropriate orientation with respect to the skin. Finally, the releasing member is operated to release the engagement between the lock mechanism and the actuator. Then, the actuator moves under the biasing force of the resilient body, and as a result, the microneedle patch is inserted into the skin.

With this applicator, the lock mechanism can keep the actuator at rest at a position where a desired biasing force is produced. That is, with this applicator, it is possible to maintain the state where the biasing force of the resilient body on the actuator is set. Thus, stable medicine administration is achieved. More specifically, the reproducibility of the load exerted by the microneedle patch to the skin is improved. In prior art, at the time when an applicator is positioned, the applicator is grasped and secured by a hand, and a spring is compressed by the other hand to produce a resilient force. According to this embodiment, however, such an operation is unnecessary. That is, according to this embodiment, the applicator can be easily operated by one hand. This provides such advantages that shaking of the applicator can be reduced, that the determination of the site to be treated by the piercing, as well as the determination of the direction for the piercing, can be performed more accurately, and that the flatness of the skin can be improved by stretching the skin by the other hand. As a result, the applicator can be more accurately and easily positioned in relation to the skin.

The lock mechanism can provide a plurality of locked states so that the magnitude of the biasing force of the resilient body can be varied.

With this applicator, the impact force exerted when the microneedle patch is inserted into the skin can be easily controlled depending on the purpose.

The actuator may have a presser part to which the microneedle patch is attached.

The main body may have an inner surface that guides the presser part so that the presser part moves along the longitudinal direction of the main body and a leading end part that extends in a direction of movement of the actuator.

With this applicator, the presser part of the actuator moves along the inner surface of the leading end part of the main body. Therefore, during the movement, the presser part is accurately kept in parallel with the surface of the skin into which the microneedle patch is pierced. Thus, the parallelism of the microneedle patch to the skin surface can be improved at the time when the microneedle patch is to be contacted with the skin, thus making it possible to pierce the microneedle patch perpendicularly into the skin and to administer the medicine with higher efficiency.

The presser part may have a base, an attachment part to which the microneedle patch is attached, and a shock-absorbing low-rigidity member disposed between the base and the attachment part.

With this applicator, since the shock-absorbing low-rigidity member is provided between the base and the attachment part, the shock-absorbing low-rigidity member allows the microneedle patch to be twisted when the presser part presses the microneedle patch against the skin, so that its flatness can be further improved. As a result, the probability that the microneedles are inserted into the skin increases.

The impacting type applicator for a microneedle patch may further comprise a biasing force imparting mechanism. The biasing force imparting mechanism may further impart a biasing force to the actuator in a state where the actuator is moved toward a leading end of the main body and thereby presses the microneedle patch against the skin.

With this applicator, after the microneedle patch is pressed against the skin, a load can be further imparted to the microneedle patch by the biasing force imparting mechanism. Thus, even if a repulsive force acts due to the resilience of the skin, the microneedles can be maintained at the depth to which the microneedles are initially inserted, and the tip end parts of the microneedles containing the medicine can be further inserted into the dermis up to an appropriate depth with reliability. As a result, the medicine can be administered to the dermis with reliability, for example.

The biasing force imparting mechanism may have a biasing force receiving part provided on the actuator and a biasing member capable of imparting a biasing force to the biasing force receiving part properly.

A leading end member according to another aspect of the present invention is a leading end member attached to an impacting type applicator that applies a microneedle patch to a skin and comprises a frame-shaped main body, a contact part, and a mount part.

The contact part is a part that is provided on the frame-shaped main body and comes into contact with the skin.

The mount part is a part that is provided on the frame-shaped main body and is detachably fitted to a leading end of the impacting type applicator.

With this leading end member, the leading end member can be attached to and detached from the impacting type applicator. Because of this, the leading end member can be replaced each time the microneedle patch is inserted into the skin. That is, the leading end member is used as a single-use disposable member. Using a new leading end member for each insertion of the microneedle patch in this way eliminates the need of the operation of sterilizing the leading end of the impacting type applicator.

The leading end member may further comprise a microneedle patch which is mounted on the frame-shaped main body.

With this leading end member, the microneedle patch is mounted on the frame-shaped main body, and hence the microneedle patch can be attached and detached along with the leading end member, so that the operation is simplified.

Effect of the Invention

With the impacting type applicator for a microneedle patch according to the present invention, the workability of a device that inserts a microneedle into a skin is improved, so that stable medicine administration is achieved.

BRIEF DESCRIPTION OF DRAWINGS

FIG. 1 is a perspective view of an impacting type applicator for a microneedle patch according to a first embodiment of the present invention.

FIG. 2 is a cross-sectional view of the applicator.

FIG. 3 is a perspective cross-sectional view of the applicator.

FIG. 4 is a cross-sectional view of the applicator.

FIG. 5 is a perspective cross-sectional view of the applicator.

FIG. 6 is a cross-sectional view of a leading end part of the applicator.

FIG. 7 is a cross-sectional view of the leading end part of the applicator.

FIG. 8 is a perspective view of an impacting type applicator for a microneedle patch according to a second embodiment of the present invention.

FIG. 9 is a cross-sectional view of a leading end part of the applicator.

FIG. 10 is a cross-sectional view of the leading end part of the applicator.

FIG. 11 is a perspective view of an impacting type applicator for a microneedle patch according to a third embodiment of the present invention.

FIG. 12 is a cross-sectional view of a leading end part of the applicator.

FIG. 13 is a cross-sectional view of the leading end part of the applicator.

FIG. 14 is a front view of the leading end part of the applicator.

FIG. 15 is a cross-sectional view of an applicator for a microneedle patch incorporated with a biasing force imparting mechanism according to a fourth embodiment of the present invention.

FIG. 16 is a cross-sectional view of the biasing force imparting mechanism incorporated with a biasing force imparting mechanism.

FIG. 17 is a graph showing a transition of administration rate of each applicator.

FIG. 18 is a photograph showing a state of a microneedle patch, after use, of a conventional applicator.

FIG. 19 is a photograph showing a state of the microneedle patch, after use, of the applicator (which performs only piercing) according to the present invention.

FIG. 20 is a photograph showing a state of the microneedle patch, after use, of the applicator (which performs piercing and pressing) according to the present invention.

FIG. 21 is a cross-sectional view of a conventional applicator.

FIG. 22 is a perspective cross-sectional view of a conventional applicator.

MODE OF CARRYING OUT THE INVENTION

1. First Embodiment (1) Overview of Configuration of Applicator

An impacting type applicator 1 for a microneedle patch (hereinafter referred to as "applicator 1") according to an embodiment of the present invention will be described with reference to FIGS. 1 to 5. FIG. 1 is a perspective view of the impacting type applicator for a microneedle patch according to a first embodiment of the present invention. FIGS. 2 and 4 are cross-sectional views of the applicator. FIGS. 3 and 5 are perspective cross-sectional views of the applicator.

The applicator 1 is a device designed to press a microneedle patch 3 (FIGS. 6 and 7) against a skin to insert a microneedle into a dermis. More specifically, the applicator 1 can produce a biasing force high enough to pierce the microneedle patch 3 into the skin.

As shown in FIGS. 6 and 7, the microneedle patch 3 has a substrate 3a and a large number of microneedles 3b formed on one surface of the substrate 3a. The microneedles 3b are a group of small protrusions. The surface of the small protrusions can be coated with a medicinal substance or the like, or the small protrusions themselves can be made of a medicinal substance. For example, the microneedle 3b may have an overall height of 30 to 1000 μm, and its side of the tip end part may be a layer of a medicine that dissolves itself in response to moisture. At the time when the microneedle 3b is inserted into the skin, only the tip end part of the microneedle is cracked, thereby leaving in the human body the tip end part to which the medicine is applied, or whole of the microneedle 3b remains in the body. The medicine is thus administered into the body.

The applicator 1 has a main body 5. The main body 5 realizes the basic configuration of the applicator 1. Specifically, the main body 5 is a cylindrical member. The main body 5 has a contact part 31 at the leading end thereof. The main body 5 has a rear end wall 33 at the rear end thereof. More specifically, the contact part 31 is a frame-shaped part that surrounds an opening at the leading end part 43 of the main body 5. The contact part has a uniform width over the entire circumference thereof. Although the opening at the leading end part 43 has a rectangular shape in this embodiment, the shape of the opening is not particularly limited. The rear end wall 33 is a wall part formed at the rear end of the main body 5 and has a through-hole 33a.

The applicator 1 has a spring expanding/compressing lever 7 (an example of actuator). The spring expanding/compressing lever 7 is attached to the main body 5 in such a manner that the spring expanding/compressing lever 7 is movable along the longitudinal direction of the main body (an axial direction of the main body 5). More specifically, the spring expanding/compressing lever 7 is disposed in the main body 5. The microneedle patch 3 can be attached to a leading end of the spring expanding/compressing lever 7. The spring expanding/compressing lever 7 extends in the main body 5 in the longitudinal direction of the main body. The rear end of the spring expanding/compressing lever 7 protrudes from the through-hole 33a in the rear end wall 33 of the main body 5. A nut 35 serving as an operation knob, for example, is fixed to the rear end of the spring expanding/compressing lever 7. The weight of the nut 35 can be increased to increase the mass of the spring expanding/compressing lever 7 and thus provide an increased impact force.

The applicator 1 has a resilient body 9. The resilient body 9 is a member that imparts a biasing force to the spring expanding/compressing lever 7. The resilient body 9 allows the microneedle 3b to be pierced into the skin to a predetermined depth with reliability. More specifically, the resilient body 9 is disposed in the main body 5 and imparts a biasing force to the spring expanding/compressing lever 7 in a state where the resilient body 9 is compressed in the vertical direction to the main body. Although the resilient body 9 is a compression coil spring in this embodiment, the type of the resilient body is not particularly limited. The resilient body may be another type of spring or an electric or pneumatic positive pressure biasing force producing device. The resilient body 9 can be compressed between the rear end wall 33 of the main body 5 and a support member 37 fixed to the spring expanding/compressing lever 7.

The applicator 1 has a lock mechanism 11. The lock mechanism 11 is a mechanism that locks the spring expanding/compressing lever 7 in a state where the resilient body 9 exerts a biasing force on the main body 5.

The applicator 1 has a piercing switch 13 (an example of the releasing member). The piercing switch 13 is a member that releases the engagement between the lock mechanism 11 and the spring expanding/compressing lever 7.

(2) Overview of Function of Applicator

A basic operation of the applicator 1 will be described with reference to FIGS. 6 and 7. FIGS. 6 and 7 are cross-sectional views of a leading end part of the applicator.

In the state shown in FIG. 6, the spring expanding/compressing lever 7 is housed in the main body 5. As shown in FIG. 7, the spring expanding/compressing lever 7 is then moved toward the leading end of the main body 5, and the microneedle patch 3 is attached to the leading end of the spring expanding/compressing lever 7. As shown in FIGS. 2 and 3, the lock mechanism 11 then locks the spring expanding/compressing lever 7 in a state where the resilient body 9 exerts a biasing force on the main body. In this state, the applicator 1 is placed at an appropriate position in an appropriate orientation with respect to the skin. Finally, the piercing switch 13 is operated to release the engagement between the lock mechanism 11 and the spring expanding/compressing lever 7. Then, as shown in FIGS. 4 and 5, the spring expanding/compressing lever 7 moves under the biasing force of the resilient body 9, and as a result, the microneedles 3b of the microneedle patch 3 are inserted into the skin.

With this applicator 1, the lock mechanism 11 can keep the spring expanding/compressing lever 7 at rest. That is, the applicator 1 can maintain the biasing force to the spring expanding/compressing lever 7 of the resilient body 9 at a predetermined state. Thus, administration of a medicine can be repeated in a stable manner under the same conditions.

More specifically, there can be improved the reproducibility of the load exerted by the microneedle patch 3 to the skin. In prior art, upon positioning of an applicator 1, a spring is compressed, e.g., by a hand to produce a resilient force. According to this embodiment, however, such operation is unnecessary. That is, according to this embodiment, the applicator 1 can be easily operated by a hand. This provides such advantages that the shaking of the applicator can be reduced, that the directioning and positioning can be performed more accurately, and that the flatness of the skin can be improved by stretching the skin by the other hand. As a result, the applicator 1 can be more accurately and easily positioned in relation to the skin. More specifically, the microneedle patch 3 can be pressed against the skin with a higher parallelism of the microneedle patch 3 to the skin.

With the improvement of the operability of the device to pierce the microneedles 3b into the skin as described above, the efficiency of administration by the microneedles 3b can be improved. For example, with a conventional product, only about 30% of the microneedles are inserted into the skin and cracked. To the contrary, there can be obtained results in accordance with this embodiment, where at least 70%, and in many cases 90% or more, of the microneedles are inserted into the skin and cracked. The reproducibility of the results is high. In other words, the amount of administration of a medicine per patch 3 can be stabilized to some extent.

In addition, since the microneedle patch 3 can be pierced into the skin while compressing the applicator 1 against the skin, the microneedles 3b can be inserted into the skin with higher reliability. In prior art, the applicator requires to be operated by both hands, it is therefore difficult to press the applicator against the skin with an appropriate biasing force.

(3) Lock Mechanism

The lock mechanism 11 can provide a plurality of locked states so that the magnitude of the biasing force of the resilient body varies. More specifically, the lock mechanism 11 has an engaging part 21 formed on the spring expanding/compressing lever 7. The engaging part 21 has a plurality of protrusions 23 serving as teeth. The plurality of protrusions 23 are formed side by side in the longitudinal direction of the main body on a surface of the spring expanding/compressing lever 7 on one side. The plurality of protrusions 23 are formed in a middle part of the spring expanding/compressing lever 7 in the longitudinal direction of the main body. The protrusion 23 has a flat surface at the leading end side, which forms a part of a plane perpendicular to the longitudinal direction of the main body, and the rear end side is inclined. Although the number of the protrusions 23 is 5 in this embodiment, the number of the protrusions 23 is typically 1 to 10, or desirably 2 to 6. It is however not particularly limited. The number of the protrusions 23 can be 1, if a fixed biasing force is to be exerted.

The lock mechanism 11 further has a claw member 25 that serves as a latch that can be engaged with the plurality of protrusions 23. As shown in FIGS. 2 to 5, the claw member 25 is a member that can abut against the flat surface of the protrusion 23. The claw member 25 can move between a first position (FIGS. 2 and 3) where the claw member 25 is engaged with the protrusion 23 to prevent the spring expanding/compressing lever 7 from moving toward the leading end and a second position (FIGS. 4 and 5) where the claw member 25 is disengaged from the protrusion 23 to allow the spring expanding/compressing lever 7 to move toward the leading end.

The position of the spring expanding/compressing lever 7 relative to the main body 5 in the longitudinal direction thereof is determined depending on with which of the protrusions 23 the claw member 25 is engaged. That is, the amount of compression of the resilient body 9 and therefore the repulsive force of the resilient body 9 depends on with which of the protrusions 23 the claw member 25 is engaged. In this embodiment, the repulsive force of the resilient body 9 can be set in a plurality of steps. More specifically, the engagement position of the spring expanding/compressing lever 7 can be changed by pinching and pulling the nut 35 provided on the rear end of the spring expanding/compressing lever 7. The spring expanding/compressing lever 7 can be moved rearward, thereby making the claw member 25 climb over the protrusions 23 one by one. In this process, the claw member 25 moves along the inclined surface of a protrusion 23, comes off the protrusion 23, and then is engaged with the next protrusion 23.

A stopper may be provided to limit rearward movement of the spring expanding/compressing lever 7 in the longitudinal direction of the main body. In that case, the repulsive force of the resilient body 9 can be preset to a value not greater than an appropriate value.

(4) Releasing Member

The piercing switch 13 is a member that releases the engagement between the lock mechanism 11 and the spring expanding/compressing lever 7. The piercing switch 13 is a member that moves the claw member 25 to separate it from the protrusion 23 of the spring expanding/compressing lever 7. More specifically, the piercing switch 13 is a switch structure that is formed on a part of the surface of the main body 5 and can be pressed down by a finger of a treating person. The piercing switch 13 has a shape extending in the longitudinal direction of the main body, and the claw member 25 is fixed to the tip end part thereof.

With the applicator 1, the impact force exerted at the time when the microneedles 3b of the microneedle patch are inserted into the skin can be easily changed depending on the purpose. For example, the biasing force is preferably set low when the skin is located close to a bone, and set high when the skin is located at a place distant from bones.

More specifically, the claw member 25 has a hole through which the spring expanding/compressing lever 7 penetrates, and has an engaging claw 25a on the edge of the hole facing the protrusion 23. The engaging claw 25a has a surface inclined toward the leading end side in the longitudinal direction of the main body, and has a flat surface, which is a part of a plane perpendicular to longitudinal direction on the main body, on the side toward the rear end in the longitudinal direction of the main body. In an engaged state, the flat surface of the engaging claw 25a is capable of abutting with the flat surface of the protrusion 23. In a moving state, the inclined surface of the engaging claw 25a is capable of abutting with the inclined surface of the protrusion 23.

More specifically, the piercing switch 13 is formed on the side of the main body 5 that is opposite to the side facing the protrusions 23 of the spring expanding/compressing lever 7. The piercing switch 13 is fixed to the main body 5 only at one end part thereof in the longitudinal direction of the main body, so that the whole of the piercing switch 13 can be elastically deformed when the other end part in the longitudinal direction of the main body is pressed down toward the spring expanding/compressing lever 7.

More specifically, the piercing switch 13 has a protrusion 13a on the surface of the end part thereof at which the claw member 25 is formed, and the protrusion 13a facilitates the pressing of the piercing switch 13 with a finger.

More specifically, the piercing switch 13 and the claw member 25 are formed as an integral member. In addition, the part of the main body 5 where the piercing switch 13 and the claw member 25 are formed is constructed as half-divided members that are separable from the other part of the main body 5 and can be attached to and detached from the other part of the main body 5.

(5) Presser Part

The spring expanding/compressing lever 7 has a presser part 41 to which the microneedle patch 3 is attached. The presser part 41 is provided at the leading end of the main body of the lever 7.

The leading end part 43 of the main body 5 extends in the direction of movement of the spring expanding/compressing lever 7 and has an inner surface 43a that substantially conforms to an outer edge of the presser part 41. Thus, the outer edge of the presser part (which has a thickness in the longitudinal direction of the main body) is guided by the inner surface 43a of the leading end part 43. In other words, the presser part 41 moves along the inner surface 43a of the leading end part 43 of the main body 5. Therefore, the presser part 41 is maintained in a proper posture during movement. As a result, the parallelism of the microneedle patch 3 to the skin is increased at the time when the microneedle patch 3 is applied to the skin, so that the uniformity of medicine administration and the efficiency of healing are improved.

As shown in FIGS. 6 and 7, the presser part 41 has a base 45. The base 45 is a plate-shaped part formed at the leading end of the spring expanding/compressing lever 7. In this embodiment, the base 45 is generally a rectangular plate.

The presser part 41 has an attachment part 47 to which the microneedle patch 3 is attached. The attachment part 47 is a plate-shaped member that is fixed to a principal surface of the base 45. The attachment part 47 is fixed to the base 45 by a screw 51. However, the method of fixing of the attachment part is not particularly limited.

The attachment part 47 is, e.g., a magnet or a magnet-containing member. The microneedle patch 3 has the substrate 3a and a large number of microneedles 3b. The substrate 3a contains a magnetic material and can be attached to and detached from the attachment part 47. For example, the substrate 3a is made of a material mixed with iron powder. In the case where no sticking material such as a film is not used as described above, impurities such as an adhesive do not come into contact with the skin.

The method of attaching/detaching the microneedle patch 3 to/from the attachment part 47 is not particularly limited. For example, an adhesive or a fixing material, such as an adhesive tape, can also be used.

Since the microneedle patch 3 has substantially the same shape (area) with the attachment part 47, the pressure on the microneedle patch 3 exerted by the biasing force 2 can be made uniform.

The presser part 41 has a low-rigidity member 49 disposed between the base 45 and the attachment part 47. The low-rigidity member 49 is a shock absorbing member. The low-rigidity member 49 has a lower rigidity than the base 45 and the attachment part 47. In other words, a low rigidity layer is present between two high rigidity layers. The low-rigidity member 49 may be a planer member or a planer member with irregularities. The low-rigidity member 49 may be composed of a combination of a plurality of different layers.

Kinds of the material constituting the low-rigidity member 49 primarily include a rubber, a sponge, a felt, and a mixture of any of a rubber, a sponge and a felt. The rubber may be a butyl rubber, an ethylene propylene rubber, an ethylene propylene diene rubber, a urethane rubber, a silicon rubber, or a fluororubber. The rubber hardness of the low-rigidity member 49 is 20 to 50, for example. The sponge may be urethane, polyethylene, or silicone. The felt may be a natural material, such as sheep wool, hair of another animal, or wool, or a synthetic fiber, such as rayon or polyester.

Since the low-rigidity member 49 is provided between the base 45 and the attachment part 47 as described above, the low-rigidity member 49 allows the microneedle patch 3 to be twisted when the presser part 41 presses the microneedle patch 3 against the skin. As a result, microneedles 3b are cracked by the distorting motion caused by the twisting, so that the ratio of the medicine-containing tip end parts remaining in the dermis of the skin in a proper manner become higher.

The presser part 41 can be placed, by the lock mechanism 11, at a plurality of insertion-ready positions in the main body 5. The presser part 41 can be placed at an insertion position that is close to the contact part 31 of the leading end part 43 of the main body 5.

In FIG. 6, the presser part 41 is placed at an insertion-ready position, and the microneedle patch 3 is yet to be attached to the presser part 41. In FIG. 7, the presser part 41 is placed at the insertion position, and the microneedle patch 3 has been attached to the presser part 41.

If the presser part 41 is made of a heavy material, or a weight is added to the presser part 41, the shaking or bounce of the whole of the applicator 1, in particular the immobile main body 5, can be prevented or reduced.

The main body 5, the spring expanding/compressing lever 7 and the like may be made, e.g., of a metal or a resin, and can be manufactured with a die, a 3D printer, a molding apparatus, or other apparatus.

2. Second Embodiment

An applicator 101 according to a second embodiment will be described with reference to FIGS. 8 to 10. FIG. 8 is a perspective view of a leading end part of the impacting type applicator for a microneedle patch according to the second embodiment of the present invention. FIG. 9 is a cross-sectional view of the leading end part of the applicator. FIG. 10 is a cross-sectional view of the leading end part of the applicator.

The applicator 101 is a device that applies a microneedle patch 103 to the skin and has basically the same structure as the applicator according to the first embodiment.

The applicator 101 has a leading end member 102, which is attached to a leading end of a main body 105.

The leading end member 102 has a frame-shaped main body 104.

The leading end member 102 has a contact part 106. The contact part 106 is a part that is provided on the frame-shaped main body 104 and is intended to come into contact with the skin. More specifically, the contact part 106 is a frame-shaped part that surrounds an opening of the frame-shaped main body 104. Although the opening of the frame-shaped main body 104 has a rectangular shape in this embodiment, the shape of the opening is not particularly limited.

The leading end member 102 has a mount part 108. The mount part 108 is provided on the frame-shaped main body 104. The mount part 108 is a part that is detachably fitted to the main body 105 of the applicator 101.

Since the leading end member 102 can be attached to and detached from the applicator 101 as described above, the leading end member 102 can be replaced each time the microneedle patch 103 is inserted into the skin. Therefore, the operation of sterilizing the leading end of the applicator 101 is unnecessary. Furthermore, one applicator 101 can be used a plurality of number of times, so that a large number of patients can be economically treated in a short time.

A structure of the mount part 108 will be specifically described. The mount part 108 is a plate-shaped part that extends in one direction from the frame-shaped main body 104. In this embodiment, a pair of mount parts 108 is provided on two opposite sides of the frame-shaped main body 104. The mount part 108 has an engaging part 108*a* shaped to project outward. On the other hand, the main body 105 has a projection 105*a* formed at a corresponding position. A side support part 105*c* is formed on both sides of the projection 105*a*.

For example, when the leading end member 102 is brought closer to the main body 105 from the state shown in FIG. 9, the mount part 108 is moved to the outer side of the leading end member 102, and then the engaging part 108*a* climbs over the projection 105*a* as shown in FIG. 10. Then, a leading end surface 105*b* of the main body 105 abuts against a seating surface 104*a* of the frame-shaped main body 104. In this way, the leading end member 102 can be attached to the main body 105.

Thus, the leading end member 102 is attached to the leading end of the main body 105 in a state where the leading end member 102 does not rattle. In addition, a force equal to or greater than a predetermined level is required to detach the leading end member 102 from the leading end of the main body 105, so that the leading end member 102 is unlikely to come off the leading end of the main body 105. In addition, the mount part 108A abuts against the side support parts 105*c*, so that the leading end member 102A does not move sideward with respect to the main body 105A.

In this embodiment, the leading end member 102 can be attached simply by squeezing the applicator 101 from above onto the leading end member 102 previously placed. That is, the workability of attachment is high.

The method of detachably attaching the leading end member to the main body is not limited to the structure according to this embodiment described above. For example, the leading end member may have a reinforcing plate that has the shape of a rectangular protrusion that is fitted into the main body of the applicator.

Although the leading end member according to this embodiment can be attached to and detached from the applicator according to the first embodiment, the leading end member can be made attachable to and detachable from an applicator having another structure.

3. Third Embodiment

An applicator 101A according to a third embodiment will be described with reference to FIGS. 11 to 13. FIG. 11 is a perspective view of a leading end part of the impacting type applicator for a microneedle patch according to the third embodiment of the present invention. FIG. 12 is a cross-sectional view of the leading end part of the applicator. FIG. 13 is a cross-sectional view of the leading end part of the applicator.

The applicator 101A is a device that applies a microneedle patch 103A to the skin, which has the same basic structure as the applicator according to the second embodiment.

The applicator 101A has a leading end member 102A, which is attached to a leading end of a main body 105A.

The leading end member 102A has a frame-shaped main body 104A.

The leading end member 102A has a contact part 106A. The contact part 106A is a part that is provided on the frame-shaped main body 104A and is intended to be contacted with the skin. More specifically, the contact part 106A is a frame-shaped part that surrounds an opening of the frame-shaped main body 104A. Although the opening of the frame-shaped main body 104A has a rectangular shape in this embodiment, the shape of the opening is not particularly limited.

The leading end member 102A has a mount part 108A. The mount part 108A is provided on the frame-shaped main body 104A. The mount part 108A is a part that is detachably fitted and fixed to the leading end of the main body 105A of the applicator 101A.

The leading end member 102A has a microneedle patch 103A attached to the frame-shaped main body 104.

The method of attaching the microneedle patch 103A will be described with reference to FIG. 14. FIG. 14 is a front view of the leading end part of the applicator. A circular or spherical protrusion 106B that extends toward the center is formed on each side of the contact part 106A. Each side of the microneedle patch 103A abuts against a corresponding one of the protrusions 106B and is supported by it. The total number of the protrusions 106B for fixation is typically 4 (one protrusion on each side). Although the total number can be 2 to 16 (0 to 4 protrusions on each side), it is desirably 2 to 4.

Such a structure facilitates attachment and detachment of the microneedle patch 103A.

Since the leading end member 102A can be attached to and detached from the applicator 101A as described above, the leading end member 102A can be replaced each time the microneedle patch 103A is inserted into the skin. Therefore, the operation of sterilizing the leading end of the applicator 101A is unnecessary. Furthermore, one applicator 101A can be used a plurality of number of times, so that the applicator 101A is economical and desirable for successive treatment of a large number of patients.

The structure of the mount part 108A will be specifically described. The mount part 108A is a plate-shaped part that extends in one direction from the frame-shaped main body 104A. In this embodiment, a pair of mount parts 108A is provided on two opposite sides of the frame-shaped main body 104A. The mount part 108A has an engaging part 108a shaped to project outward. On the other hand, the main body 105A has a projection 105a formed at a corresponding position. A side support part 105c is formed on both sides of the projection 105a.

For example, when the leading end member 102A is brought closer to the main body 105A from the state shown in FIG. 12, the mount part 108A is moved to the outer side of the leading end member 102A, and then the engaging part 108a climbs over the projection 105a as shown in FIG. 13. Then, a leading end surface 105b of the main body 105 abuts against a seating surface 104a of the frame-shaped main body 104A. In this way, the leading end member 102A can be attached properly to the main body 105A.

Thus, the leading end member 102A is attached to the leading end of the main body 105A in a state where the leading end member 102A does not rattle. Since a force greater than a predetermined force is required to detach the leading end member 102A from the leading end of the main body 105A, the leading end member 102A is less likely to drop off from the leading end of the main body 105A. In addition, the leading end member 102A is fixed not to move sideward with respect to the main body 105A because the mount part 108A abuts against the side support parts 105c.

Since the microneedle patch 103A is mounted on the frame-shaped main body 104A as described above, the microneedle patch 103A can be attached and detached along with the leading end member 102A, and thus the operation is simplified. In particular, in this embodiment, a hand of a person does not come into contact with the surface of the microneedle patch 103A on which the microneedles 103b are formed, so that the sterile condition of the microneedle patch 103A is maintained.

In addition, in this embodiment, the attachment part 47 does not need to be a magnet or to contain a magnet. Furthermore, the substrate 103a of the microneedle patch 103A does not need to be mixed with iron powder or the like.

In this embodiment, the leading end member 102A can be attached simply by pushing the applicator 101A from above onto the previously placed leading end member 102A. That is, the workability of attachment is high. Furthermore, it is possible to prepare a fitting-type leading end member having the same width and comprising two to twelve or more microneedle patches coupled side by side to each other. This makes it possible to perform successive and repeating administration by, after fitting the microneedle patches, sliding the microneedle patches sideward from one end of it.

The microneedle patches can be coupled in the state of a row, a semicircle, a circle, or a sphere. As an alternative, microneedle patches can be fixed onto a belt-like member and the piercing can be performed successively by moving the belt-like member. In this case, microneedle patches can be fixed onto a belt-shaped support, so that each microneedle patch can be moved and repositioned, and then pierced into the skin. The microneedle patches can be actuated manually, electrically, pneumatically or otherwise.

Alternatively, a plurality of microneedle patches can be housed in an applicator in a state stacked on one another with a spacer interposed between every two of the microneedle patches, and the microneedle patches can be successively pierced into the skin beginning with the lowermost microneedle patch. In that case, the spacer may be a frame-shaped object or may be integrated with the microneedle patch.

While the microneedle patch 103 is fixed at a position extremely close to the skin, the spring expanding/compressing lever 7 directly hits the back surface of the microneedle patch to allow the tip end parts of the microneedles 103b penetrate into the dermis through the epidermis and remain there. Because of this, the microneedles 103b are unlikely to tilt before they reach the skin at the time when the microneedle patch 103 is pierced. That is, the parallelism between the skin surface and the patch surface is improved, and since the microneedles 103b are perpendicularly inserted into the skin surface, the medicine can be administered from the microneedles 103b into the dermis with higher reliability.

The method of detachably attaching the leading end member to the main body is not limited to the structure according to the embodiments described above.

Although the leading end member according to this embodiment can be attached to and detached from the applicator according to the first embodiment, the leading end member can also be made attachable to and detachable from an applicator having another structure.

4. Fourth Embodiment

An applicator 1 according to a fourth embodiment will be described with reference to FIGS. 15 and 16. FIGS. 15 and 16 are cross-sectional views of the impacting type applicator for a microneedle patch that incorporates a biasing force imparting mechanism according to the fourth embodiment of the present invention.

The applicator 1 is a device that applies a microneedle patch 3 to the skin and has basically the same structure as the applicator according to the first embodiment.

The impacting type applicator 1 for a microneedle patch has a biasing force imparting mechanism 121. The biasing force imparting mechanism 121 is a mechanism that imparts a biasing force to the spring expanding/compressing lever 7 in a state where the presser part 41 is moved to the leading end of the main body 5 to press the microneedle patch 3 against the skin.

With this applicator 1, after the microneedle patch 3 is pressed against the skin, a load can be re-applied to the microneedle patch by the biasing force imparting mechanism 121 which strongly presses the main body of the applicator against the skin. Thus, even if a repulsive force acts due to the resilience of the skin, the microneedles can be maintained at the depth to which the microneedles are initially inserted, and the tip end parts of the microneedles can be further inserted into a deeper part of the dermis and can be made to crack and remain there. It is therefore possible to administer, e.g., a medicine to the dermis with reliability. In this embodiment, it is expected that the medicine applied to the microneedles is readily and stably administered into the dermis, and that the medicine administered through the dermis, in particular, through the network of capillary vessels in the dermal papillary layer can be absorbed into the blood vessels of the whole body, thereby producing the desired medical effect. Furthermore, if a method of administering an immune sensitizing substance, such as a vaccine, into the dermis or the papillary layer directly below the dermis is established according to this embodiment, it will be possible to establish a technique that would enable easy, reliable and quick acquisition of immunity with a vaccine.

The biasing force imparting mechanism 121 has a biasing force receiving part 123 provided on the spring expanding/compressing lever 7, and a claw member 25 serving as a biasing member capable of imparting a biasing force to the biasing force receiving part 123 acting as a linear cam. The biasing force receiving part 123 is formed at the rear of the protrusions 23 in the longitudinal direction of the main body. As with the protrusion 23, the biasing force receiving part 123 has a flat surface, which forms a part of a plane perpendicular to the longitudinal direction of the main body, on the side toward the leading end, and has an inclined surface on the side toward the rear end. As shown in FIG. 16, the biasing force receiving part 123 is provided at a position corresponding to the place where the claw member 25 is positioned, at the time when the engagement between the lock mechanism 11 and the spring expanding/compressing lever 7 is released by the piercing switch 13 and the spring expanding/compressing lever 7 moves to the position closest to the leading end.

In this embodiment, the spring expanding/compressing lever 7 is moved toward the leading end of the main body 5, and the microneedle patch 3 is attached to the leading end of the spring expanding/compressing lever 7. Then, as shown in FIG. 15, the lock mechanism 11 locks the spring expanding/compressing lever 7 in a state where the resilient body 9 exerts the biasing force on the main body. In this state, the applicator 1 is placed at an appropriate position in an appropriate orientation with respect to the skin. Finally, the piercing switch 13 is operated to release the engagement between the lock mechanism 11 and the spring expanding/compressing lever 7. Then, as shown in FIG. 16, the spring expanding/compressing lever 7 moves under the biasing force of the resilient body 9, and as a result, the microneedles 3b of the microneedle patch 3 are inserted into the skin.

In the state shown in FIG. 16, the biasing force receiving part 123 is located at a position corresponding to the claw member 25. Once the finger is removed from the piercing switch 13, the engaging claw 25a of the claw member 25 is fixed again to the biasing force receiving part 123 under the resilient force of the piercing switch 13, and the biasing force imparting mechanism 121 biases the spring expanding/compressing lever 7 (secondary pressing). Thus, a force component toward the leading end in the longitudinal direction of the main body acts on the spring expanding/compressing lever 7, so that the presser part 41 further presses the microneedle patch 3 against the skin. In this way, the presser part 41 pierces the microneedle patch 3 into the skin under the biasing force of the resilient body 9 (primary pressing), and then the claw member 25 further applies a load to make the presser part 41 firmly press the microneedle patch 3 against the skin (secondary pressing) and acting as a damper of rearward motion, whereby the microneedles are inserted further into the dermis and the tip ends of the microneedles with the medicine applied thereto are cracked there. Thus, the advantageous effects described above can be achieved.

As a modification of this embodiment, the load on the biasing force receiving part 123 applied by the resilient force of the claw member 25 may be set low or close to zero, and an operator may press the claw member 25 with a finger to make the presser part 41 produce a pressing load on the microneedle patch 3 as a part of the biasing force imparting mechanism.

In another modification, the load on the biasing force receiving part 123 applied by the claw member 25 may be set at a proper value, and an operator may press the claw member 25 with a finger to increase the pressing load on the microneedle patch 3 applied by the presser part 41.

In still another modification, there may be used a biasing member having a structure different from those described above, including, e.g., a coil spring other than the claw structure, a plate spring, a rubber molded article, or an actuator. Moreover, in cases where a biasing member having a different structure is used, there may be employed a mechanism in which a pressing load can be produced with a finger of an operator in a similar manner as described above.

Example

An example will be described with reference to FIGS. 17 to 20. FIG. 17 is a graph showing a transition of the administration rate of each applicator. FIG. 18 is a photograph showing the state of the microneedle patch of a conventional applicator after use. FIG. 19 is a photograph showing the state of the microneedle patch (after use) of an applicator (which performed only piercing) according to the present invention. FIG. 20 is a photograph showing the state of the microneedle patch (after use) of an applicator (which performed piercing and secondary pressing) according to the present invention.

In the example, experiments were performed using the three types of applicators described below, and the results were compared. The basic structures of the main body, the resilient member, the spring expanding/compressing lever and the needle patch of each applicator were common.

<1> Conventional applicator (corresponding to the conventional technique shown in FIGS. 21 and 22)

<2> Applicator with the lock mechanism (corresponding to the first to third embodiments)

<3> Applicator with the biasing force imparting mechanism (corresponding to the fourth embodiment)

<1> Conventional Applicator

As shown in FIG. 17, with the conventional applicator, the microneedles did not crack uniformly over the patch, and in many cases cracked microneedles distributed unevenly. In addition, the percentage of the cracked microneedles per patch, which is referred to as administration rate, was as low as 30% or less, and the height of cracked position of the microneedles, which is referred to as height of break, was also as low as 182.9 µm on average, compared with the total height of about 550 µm. This is not preferable for the purpose of piercing the microneedles into the dermis layer with reliability.

Furthermore, as shown in FIG. 18, with the conventional applicator, the remaining microneedles were tall, and the height of break was not uniform over the entire patch.

<2> Applicator with Lock Mechanism

As shown in FIG. 17, with the applicator having the lock mechanism (which performs only piercing), it was confirmed that the uniformity of cracking of the microneedles on the microneedle patch was improved because the microneedles were able to be perpendicularly pierced into the skin. As a result, the administration rate was improved to 70%, and the height of break was also improved to 262.5 μm on average. Thus, the medicine was able to be administered with higher reliability into the dermis layer to a greater depth.

Furthermore, as shown in FIG. 19, it was confirmed that the height of break of the microneedles increased, and the microneedles cracked with improved uniformly as a whole. However, as shown in the elliptic frame in FIG. 19, it was also confirmed that microneedles did not crack in part of areas, e.g., in part of outer peripheral area.

<3> Applicator with Biasing Force Imparting Mechanism

As shown in FIG. 17, with the applicator having the biasing force imparting mechanism (which performs piercing and pressing), since the needles were further pressed in the secondary pressing after the needles were pierced into the skin, the needles cracked more uniformly, and the administration rate was 95% (a higher value). The height of break was 310.2 μm, which shows that the needles cracked at positions closer to their respective roots.

Furthermore, as shown in FIG. 20, more needles were cracked in the outer peripheral area and the uniformity of the piercing was also improved, compared with FIG. 19.

5. Characteristics of Embodiments

The impacting type applicator 1 for a microneedle patch (which is an example of the impacting type applicator for a microneedle patch) is an applicator that applies the microneedle patch 3 (which is an example of the microneedle patch) to the skin and comprises the main body 5 (which is an example of the main body), the spring expanding/compressing lever 7 (which is an example of the actuator), the resilient body 9 (which is an example of the resilient body), the lock mechanism 11 (which is an example of the lock mechanism), and the piercing switch 13 (which is an example of the releasing member). The spring expanding/compressing lever 7 is movably attached to the main body 5, and the microneedle patch 3 can be attached to the leading end of the spring expanding/compressing lever 7. The resilient body 9 is a member that imparts a biasing force to the spring expanding/compressing lever 7. The lock mechanism 11 is a mechanism that locks the actuator in a state where the resilient body 9 can exert the biasing force on the main body 5. The piercing switch is a member that releases the engagement between the lock mechanism 11 and the spring expanding/compressing lever 7.

6. Other Embodiments

Although a plurality of embodiments of the present invention have been described above, the present invention is not limited to the embodiments described above, and various modifications can be made without departing from the spirit of the present invention. In particular, the plurality of embodiments and modifications described in this specification can be arbitrarily combined with each other as required.

It is a matter of course that the first embodiment and the second embodiment can be combined with each other, and the first embodiment and the third embodiment can be combined with each other. Furthermore, the fourth embodiment can be combined with the second embodiment or the third embodiment.

INDUSTRIAL APPLICABILITY

The present invention can be applied to a wide variety of impacting type applicators for a microneedle patch and leading end members thereof.

EXPLANATION OF LETTERS OR NUMERALS

1: impacting type applicator for microneedle patch
3: microneedle patch
3a: substrate
3b: microneedle
5: main body
7: spring expanding/compressing lever
9: resilient body
11: lock mechanism
13: piercing switch
21: engaging part
23: protrusion
25: claw member
31: contact part
33: rear end wall
33a: hole
35: nut
37: support member
41: presser part
43: leading end part
43a: inner surface
45: base
47: attachment part
49: low-rigidity member
51: screw
101: applicator
101A: applicator
102: leading end member
102A: leading end member
103: microneedle patch
103A: microneedle patch
103a: substrate
103b: microneedle
104: frame-shaped main body
104A: frame-shaped main body
104a: seating surface
105: main body
105A: main body
105a: projection
105b: leading end surface
106: contact part
106A: contact part
108: mount part
108A: mount part
108a: engaging part
121: biasing force imparting mechanism
123: biasing force receiving part

The invention claimed is:
1. An impacting type applicator that applies a microneedle patch to a skin by pressing the microneedle patch against the skin, comprising:
   a main body;
   an actuator that is movably attached to the main body, and that has a leading end for attaching to the microneedle patch;

a resilient body that imparts a biasing force to the actuator;

a lock mechanism that locks the actuator in a state where the resilient body exerts the biasing force on the main body; and a releasing member that releases the lock mechanism, and a biasing force imparting mechanism that imparts a further biasing force to the actuator in a state where the actuator is moved toward a leading end part of the main body and thereby presses the microneedle patch against the skin.

2. The impacting type applicator for a microneedle patch according to claim 1, wherein the lock mechanism can realize a plurality of locked states to vary magnitude of the biasing force of the resilient body.

3. The impacting type applicator for a microneedle patch according to claim 2, wherein the actuator has a presser part to which the microneedle patch is attached, and the main body has an inner surface that guides the presser part so that the presser part moves along the longitudinal direction of the main body and a leading end part that extends in a direction of movement of the actuator.

4. The impacting type applicator for a microneedle patch according to claim 1, wherein the actuator has a presser part to which the microneedle patch is attached, and the main body has an inner surface that guides the presser part so that the presser part moves along the longitudinal direction of the main body and a leading end part that extends in a direction of movement of the actuator.

5. The impacting type applicator for a microneedle patch according to claim 4, wherein the presser part has a base, an attachment part to which the microneedle patch is attached, and a shock-absorbing low-rigidity member located between the base and the attachment part.

6. The impacting type applicator for a microneedle patch according to claim 1, wherein the biasing force imparting mechanism has a biasing force receiving part provided on the actuator and a biasing member that imparts the further biasing force to the biasing force receiving part.

7. A leading end member attached to the impacting type applicator according to claim 1 that applies a microneedle patch to a skin, comprising:

a frame-shaped main body;

a contact part that is provided on the frame-shaped main body and comes into contact with the skin; and a mount part that is provided on the frame-shaped main body and is intended to be detachably fitted to a leading end of the impacting type applicator.

8. The leading end member according to claim 7, further comprising the microneedle patch, the microneedle patch being mounted on the frame-shaped main body.

9. An impacting type applicator that applies a microneedle patch to a skin by pressing the microneedle patch against the skin, comprising:

a main body;

a piston that is movably attached to the main body, and that has a leading end configured to attach to the microneedle patch;

a resilient body that imparts a biasing force to the piston;

a lock configured to lock the piston in a position where the resilient body exerts the biasing force on the main body; and a trigger configured to release the lock thereby allowing the piston to move in a forward motion in response to the biasing force imparted by the resilient body, and a linear cam configured to impart forward motion to the piston after the leading end presses the microneedle patch against the skin.

10. The impacting type applicator for a microneedle patch according to claim 9, wherein the piston is configured to have a plurality of locked positions to vary magnitude of the biasing force of the resilient body.

11. The impacting type applicator for a microneedle patch according to claim 10, wherein the leading end of the piston has a supporting surface configured to support the microneedle patch, and the main body has an inner surface configured to guide the leading end of the piston so that the microneedle patch translationally moves toward the leading end of the main body.

12. The impacting type applicator for a microneedle patch according to claim 10, further comprising a damper configured to impede rearward motion of the piston after the leading end presses the microneedle patch against the skin.

13. The impacting type applicator for a microneedle patch according to claim 9, wherein the leading end of the piston has a supporting surface configured to support the microneedle patch, and the main body has an inner surface configured to guide the leading end of the piston so that the microneedle patch moves in a forward motion to a leading end of the main body.

14. The impacting type applicator for a microneedle patch according to claim 13, wherein the piston further comprises a coupling at the leading end configured to releasably attach the microneedle patch.

15. The impacting type applicator for a microneedle patch according to claim 13, wherein the piston further comprises a shock-absorbing low-rigidity section adjacent the supporting surface.

16. A leading end member attached to the impacting type applicator of claim 9 that applies a microneedle patch to a skin, comprising:

a frame-shaped main body comprising a contact part that comes into contact with the skin during use; and a mount part that is provided on the frame-shaped main body and is configured to be detachably fitted to a leading end of the main body of the impacting type applicator.

17. The leading end member according to claim 16, further comprising the microneedle patch framed by the frame-shaped main body, wherein the leading end member is configured so that the microneedle patch attaches to the leading end of the piston during loading of the impacting type applicator.

18. The impacting type applicator for a microneedle patch according to claim 9, further comprising a damper configured to impede rearward motion of the piston after the leading end presses the microneedle patch against the skin.

* * * * *